United States Patent
De Groot et al.

(10) Patent No.: US 7,106,454 B2
(45) Date of Patent: Sep. 12, 2006

(54) PROFILING COMPLEX SURFACE STRUCTURES USING SCANNING INTERFEROMETRY

(75) Inventors: Peter J. De Groot, Middletown, CT (US); Robert Stoner, Chester, CT (US); Xavier Colonna De Lega, Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 339 days.

(21) Appl. No.: 10/795,808

(22) Filed: Mar. 8, 2004

(65) Prior Publication Data

US 2005/0073692 A1 Apr. 7, 2005

Related U.S. Application Data

(60) Provisional application No. 60/539,437, filed on Jan. 26, 2004, provisional application No. 60/452,615, filed on Mar. 6, 2003, provisional application No. 60/452,465, filed on Mar. 6, 2003.

(51) Int. Cl.
*G01B 11/02* (2006.01)
(52) U.S. Cl. ..................... 356/511; 356/497
(58) Field of Classification Search ............ 356/497, 356/503, 511, 512, 513, 514, 516
See application file for complete search history.

(56) References Cited

U.S. PATENT DOCUMENTS

| | | | |
|---|---|---|---|
| 4,576,479 A | 3/1986 | Downs | 356/351 |
| 4,660,980 A | 4/1987 | Takabayashi et al. | |
| 4,818,110 A | 4/1989 | Davidson | |
| 4,999,014 A | 3/1991 | Gold et al. | 356/382 |
| 5,042,949 A | 8/1991 | Greenberg et al. | |
| 5,042,951 A | 8/1991 | Gold et al. | |
| 5,112,129 A | 5/1992 | Davidson et al. | |
| 5,129,724 A | 7/1992 | Brophy et al. | 356/357 |
| 5,133,601 A | 7/1992 | Cohen et al. | 356/359 |
| 5,135,307 A | 8/1992 | de Groot et al. | |
| 5,301,010 A | 4/1994 | Jones et al. | |
| 5,398,113 A | 3/1995 | de Groot | 356/360 |
| 5,587,792 A | 12/1996 | Nishizawa et al. | 355/356 |
| 5,589,938 A * | 12/1996 | Deck | 356/497 |
| 5,602,643 A | 2/1997 | Barrett | 356/360 |
| 5,900,633 A | 5/1999 | Solomon et al. | 250/339.08 |
| 6,242,739 B1 | 6/2001 | Cherkassky | 250/339.11 |
| 6,249,351 B1 | 6/2001 | de Groot | |
| H1972 H | 7/2001 | Inoue | |
| 6,259,521 B1 | 7/2001 | Miller et al. | |
| 6,377,349 B1 | 4/2002 | Fercher | |

(Continued)

FOREIGN PATENT DOCUMENTS

DE 4108944 9/1992

(Continued)

OTHER PUBLICATIONS

Dresel, Thomas et al., "Three-dimensional sensing of rough surfaces by coherence radar", *Applied Optics*, vol. 31, No. 7, pp. 919-925 (Mar. 1, 1992).

(Continued)

*Primary Examiner*—HWA (Andrew) Lee
*Assistant Examiner*—Michael A. Lyons
(74) *Attorney, Agent, or Firm*—Fish & Richardson P.C.

(57) ABSTRACT

A method including comparing information derivable from a scanning interferometry signal for a first surface location of a test object to information corresponding to multiple models of the test object, wherein the multiple models are parametrized by a series of characteristics for the test object. The derivable information being compared may relate to a shape of the scanning interferometry signal for the first surface location of the test object.

71 Claims, 17 Drawing Sheets

U.S. PATENT DOCUMENTS

| | | | |
|---|---|---|---|
| 6,417,109 B1 * | 7/2002 | Jordan et al. | 438/692 |
| 6,500,591 B1 | 12/2002 | Adams | |
| 6,507,405 B1 | 1/2003 | Grek et al. | |
| 6,545,763 B1 | 4/2003 | Kim et al. | 356/503 |
| 6,597,460 B1 | 7/2003 | Groot et al. | 356/512 |
| 6,721,094 B1 | 4/2004 | Sinclair et al. | |
| 6,940,604 B1 | 9/2005 | Jung et al. | |
| 2002/0135775 A1 | 9/2002 | de Groot et al. | |
| 2002/0196450 A1 | 12/2002 | Olszak et al. | |
| 2003/0112444 A1 | 6/2003 | Yang et al. | |
| 2004/0085544 A1 | 5/2004 | de Groot et al. | |
| 2004/0189999 A1 | 9/2004 | de Groot et al. | |
| 2005/0057757 A1 | 3/2005 | de Lega et al. | |
| 2005/0068540 A1 | 3/2005 | de Groot et al. | |
| 2005/0078318 A1 | 4/2005 | de Groot | |
| 2005/0078319 A1 | 4/2005 | de Groot | |
| 2005/0088663 A1 | 4/2005 | de Groot et al. | |
| 2005/0146727 A1 | 7/2005 | Hill | |
| 2005/0237534 A1 | 10/2005 | Deck | |
| 2006/0012582 A1 | 1/2006 | de Lega | |

FOREIGN PATENT DOCUMENTS

| | | |
|---|---|---|
| DE | 4309056 | 9/1994 |
| EP | 0 397 388 A2 | 11/1990 |
| EP | 0 549 166 A2 | 6/1993 |
| EP | 0 617 255 A1 | 9/1994 |
| EP | 0 929 094 A2 | 7/1999 |
| GB | 2385417 | 8/2003 |
| WO | WO 97/44633 | 11/1997 |
| WO | WO 02/082008 | 10/2002 |
| WO | WO 03/062802 | 7/2003 |

OTHER PUBLICATIONS

Feke, Gilbert D. et al., "Interferometric back focal plane microellipsometry", Applied Optics, vol. 37, No. 10, pp. 1796-1802 (Apr. 1, 1998).

Kim, Seung-Woo et al., "Thickness-profile measurement of transparent thin-film layers by white-light scanning interferometry", Applied Optics, vol. 38, No. 28, pp. 5968-5973 (Oct. 1, 1999).

Kino, Gordon S. et al., "Mirau correlation microscope", Applied Optics, vol. 29, No. 26, pp. 3775-3783 (Sep. 10, 1990).

Pelligrand, S. et al., "Mesures 3D de topographies et de vibrations a l'echelle (sub)micrometrique par microscopie optique interferometrique", Proc. Club CMOI, Methodes et Techniques Optiques pour l'Industrie (2002).

Pluta, Maksymilian, "Advanced Light Microscopy", vol. 3, (Elsevier, Amsterdam, 1993) pp. 265-271.

Rosencwaig, Allan et al., "Beam profile reflectometry: A new technique for dielectric film measurements", Applied Physics Letters, vol. 60, No. 11, pp. 1301-1303 (Mar. 16, 1992).

Sandoz, Patrick "Wavelet transform as a processing tool in white-light interferometry", Optics Letters, vol. 22, No. 14, pp. 1065-1067 (Jul. 15, 1997).

Shatalin, S.V. et al., "Reflection conoscopy and micro-ellipsometry of isotropic thin film structures", Journal of Microscopy, vol. 179, Part 3, pp. 241-252 (Sep. 1995).

C. Akcay et al., "Spectral shaping to improve the point spread function in optical coherence tomography", Optics Letters, vol. 28, No. 20, pp. 1921-1923 (Oct. 15, 2003).

R.M.A. Azzam et al., "Reflection and Transmission of Polarized Light by Stratified Planar Structures", Ellipsometry and Polarized Light, Elsevier Science B.V. ISBN 0 444 87016 4 (Paperback) pp. 267-363 (1987).

R.M.A. Azzam et al, "Ellipsometric function of a film-substrate system: Applications to the design of reflection-type optical devices and to ellipsometry", Journal of the Optical Society of America, vol. 5, No. 3, pp. 252-260.

M. Bashkansky et al., "Signal Processing for Improving Field Cross-correlation Function in Optical Coherence Tomography", Supplement to Optics & Photonics News, 9(5) (May 1998).

Berman et al., "Review of In Situ & In-line Detection for CMP Applications", Semiconductor Fabtech—8th Edition, pp. 267-274.

A. Bosseboeuf et al., "Application of microscopic interferometry techniques in the MEMS field", Proc. SPIE, 5145, pp. 1-16 (2003).

M. Davidson et al., "An Application of Interference Microscopy to Integrated Circuit Inspection and Metrology", Proceedings of SPIE, vol. 775, pp. 233-247 (1987).

J.E. Greivenkamp, "Generalized data reduction for heterodyne interferometry", Opt. Eng., vol. 23 No. 4, pp. 350-352 (Jul./Aug. 1984).

P de Groot et al., "Signal modeling for low coherence height-scanning interference microscopy", Applied Optics, vol. 43 No. 25, pp. 4821-4830 (Sep. 1, 2004).

P. de Groot, "Derivation of algorithms for phase-shifting interferometry using the concept of a data-sampling window", Appl. Opt., 34(22), p. 4723-4730 (1995).

P. de Groot et al., "Signal modeling for modern interference microscopes", SPIE Proceedings, 5457-4 (2004).

Peter de Groot et al., "Determination of fringe order in white-light interference microscopy", Appl. Opt., 41(22) pp. 4571-4578 (2002).

P.A. Flournoy et al., "White-light interferometric thickness gauge", Appl. Opt., 11(9), pp. 1907-1915 (1972).

G. Hausler et al., "Coherence Radar and Spectral Radar—New Tools for Dermatological Diagnosis", Journal of Biomedical Optics, vol. 3, No. 1, pp. 21-31 (Jan. 1998).

R.D. Holmes et al., "Scanning microellipsometry for extraction of true topograpy", Electronics Letters, vol. 31, No. 5, pp. 358-359 (Mar. 2, 1995).

Seung-Woo Kim et al., "Thickness-profile measurement of transparent thin-film layers by white-light scanning interferometry", Applied Optics, vol. 38, No. 28, pp. 5968-5973 (Oct. 1, 1999).

Kieran G. Larkin, "Efficient nonlinear algorithm for envelope detection in white light interferometry", J. Opt. Soc. Am A4, pp. 832-843 (1996).

Kujawinska, Malgorzata, "Spatial Phase Measurement Methods", Interferogram Analysis: Digital Fringe Pattern Measurement Techniques, IOP Publishing Ltd. 1993, pp. 141-193.

Lee et al., "Profilometry with a coherence scanning microscope", Appl. Opt., 29(26), pp. 3784-3788 (1990).

I. Lee-Bennett, "Advances in non-contacting surface metrology", OF&T Workshop, paper OTuC1 (2004).

K. Leonhardt et al., "Micro-Ellipso-Height-Profilometry", Optics Communications, vol. 80, No. 3, 4, pp. 205-209 (Jan. 1, 1991).

Y. Liu et al., "Common path interferometric microellipsometry", SPIE, vol. 2782, pp. 635-645 (1996).

Lyakin et al., "The interferometric system with resolution better than coherence length for determination of geometrical thickness and refractive index of a layer object", Proceedings of the SPIE—The International Society for Optical Engineering SPIE-INT. Soc. Opt. Eng USA, vol. 4956, pp. 163-169 (Jul. 2003).

C.J. Morgan, "Least-Squares estimation in phase-measurement interferometry", Apt. Let., 7(8), pp. 368-370 (1982).

Ngoi et al., "Phase-shifting interferometry immune to vibration", Applied Optics, vol. 40, No. 19, pp. 3211-3214 (2001).

A.V. Oppenheim et al., "10.3: The time-dependent Fourier Transform", Discrete-Time Signal Processing, 2nd Edition, pp. 714-722 (Prentice Hall, New Jersey, 1999).

M.C. Park et al., "Direct quadratic polynomial fitting for fringe peak detection of white light scanning interferograms", Opt. Eng, 39(4), pp. 952-959 (2000).

W.H. Press et al., "Linear Correlation", Numerical Recipes in C, Cambridge University Press, 2nd Edition, pp. 636-639 (1992).

P. Sandoz et al., "Optical implementation of frequency domain analysis for white light interferometry", Proceedings SPIE, vol. 2545, pp. 221-228 (Jun. 1995).

P. Sandoz et al., "High-resolution profilometry by using phase calculation algorithms for spectroscopic analysis of white-light interferograms", Journal of Modern Optics, vol. 43, No. 4, pp. 701-708 (1996).

P. Sandoz et al., "Processing of white light correlograms: simultaneous phase and envelope measurements by wavelet transformation", SPIE, 3098, pp. 73-82 (1997).

U. Schnell et al., "Dispersive white-light interferometry for absolute distance measurement with dielectric multilayer systems on the target", *Optics Letters,* vol. 21, No. 7, pp. 528-530 (Apr. 1996).

J. Schwider et al., "Dispersive interferometric profilometer", *Optics Letters,* vol. 19, No. 13, pp. 995-997 (Jul. 1994).

C.W. See et al., "Scanning optical microellipsometer for pure surface profiling", *Applied Optics,* vol. 35, No. 34, pp. 6663-6668 (Dec. 1, 1996).

M. Totzeck, "Numerical simulation of high-NA quantitative polarization microscopy and corresponding near-fields", *Optik,* vol. 112, No. 9, pp. 399-406 (2001).

R. Tripathi et al., "Spectral shaping for non-Gaussian source spectra in optical coherence tomography", *Optics Letters,* vol. 27, No. 6, pp. 406-408 (2002).

D. Willenborg et al., "A novel micro-spot dielectric film thickness measurement system", *SPIE,* vol. 1594, pp. 322-333 (1991).

\* cited by examiner

PROFILING COMPLEX SURFACE STRUCTURES USING SCANNING INTERFEROMETRY

CROSS-REFERENCE TO RELATED APPLICATIONS

This application claims priority under 35 U.S.C. 119(e) to the following U.S. Provisional Patent Applications: U.S. Patent Application Ser. No. 60/452,615 filed Mar. 6, 2003 and entitled "PROFILING COMPLEX SURFACE STRUCTURES USING HEIGHT SCANNING INTERFEROMETRY," U.S. Patent Application Ser. No. 60/452,465 filed Mar. 6, 2003 and entitled "PROFILING COMPLEX SURFACE STRUCTURES USING SIGNALS FROM HEIGHT SCANNING INTERFEROMETRY," and U.S. Patent Application Ser. No. 60/539,437 filed Jan. 26, 2004 and entitled "SURFACE PROFILING USING AN INTERFERENCE PATTERN MATCHING TEMPLATE," all of which are incorporated herein by reference.

BACKGROUND

The invention relates to using scanning interferometry to measure surface topography and/or other characteristics of objects having complex surface structures, such as thin film(s), discrete structures of dissimilar materials, or discrete structures that are underresolved by the optical resolution of an interference microscope. Such measurements are relevant to the characterization of flat panel display components, semiconductor wafer metrology, and in-situ thin film and dissimilar materials analysis.

Interferometric techniques are commonly used to measure the profile of a surface of an object. To do so, an interferometer combines a measurement wavefront reflected from the surface of interest with a reference wavefront reflected from a reference surface to produce an interferogram. Fringes in the interferogram are indicative of spatial variations between the surface of interest and the reference surface.

A scanning interferometer scans the optical path length difference (OPD) between the reference and measurement legs of the interferometer over a range comparable to, or larger than, the coherence length of the interfering wavefronts, to produce a scanning interferometry signal for each camera pixel used to measure the interferogram. A limited coherence length can be produced, for example, by using a white-light source, which is referred to as scanning white light interferometry (SWLI). A typical scanning white light interferometry (SWLI) signal is a few fringes localized near the zero optical path difference (OPD) position. The signal is typically characterized by a sinusoidal carrier modulation (the "fringes") with bell-shaped fringe-contrast envelope. The conventional idea underlying SWLI metrology is to make use of the localization of the fringes to measure surface profiles.

SWLI processing techniques include two principle trends. The first approach is to locate the peak or center of the envelope, assuming that this position corresponds to the zero optical path difference (OPD) of a two-beam interferometer for which one beam reflects from the object surface. The second approach is to transform the signal into the frequency domain and calculate the rate of change of phase with wavelength, assuming that an essentially linear slope is directly proportional to object position. See, for example, U.S. Pat. No. 5,398,113 to Peter de Groot. This latter approach is referred to as Frequency Domain Analysis (FDA).

Unfortunately such assumptions may break down when applied to a test object having a thin film because of reflections by the top surface and the underlying film/substrate interface. Recently a method was disclosed in U.S. Pat. No. 6,545,763 to S. W. Kim and G. H. Kim to address such structures. The method fit the frequency domain phase profile of a SWLI signal for the thin film structure to an estimated frequency domain phase profile for various film thicknesses and surface heights. A simultaneous optimization determined the correct film thickness and surface height.

SUMMARY

The inventors have realized that there is a wealth of information in a scanning interfometry signal, much of which is ignored in conventional processing. While complex surface structures, such as thin films, may corrupt conventional processing techniques based on identifying the location of the peak in the fringe contrast envelope or calculating a slope for the frequency domain phase profile, new processing techniques disclosed herein can extract surface height information and/or information about that the complex surface structure.

For example, while not assuming that the surface height information is directly related to the peak in the fringe contrast envelope, some embodiments of the invention assume that a change in surface height translates the scanning interferometry signal with respect to a reference scan position, but otherwise preserves the shape of the scanning interferometry signal. Thus, the shape of the scanning interferometry signal is especially useful in characterizing complex surface structure because it is independent of surface height. Similarly, in the frequency domain, some embodiments assume a change in surface height introduces a linear term in the frequency domain phase profile, even though the frequency domain profile itself may not be linear. However, the change in surface height leaves the frequency domain amplitude profile unchanged. Therefore, the frequency domain amplitude profile is especially useful in characterizing complex surface structure.

After the complex surface structure is characterized, surface height can be efficiently determined. For example, a cross-correlation between the scanning interferometry signal and a model signal having the shape corresponding to the complex surface structure can produce a peak at a scan coordinate corresponding to the surface height. Similarly, in the frequency domain, a phase contribution resulting from the complex surface structure can be subtracted from the frequency domain phase profile and the surface height can be extracted using a conventional FDA analysis.

Examples of complex surface structure include: simple thin films (in which case, for example, the variable parameter of interest may be the film thickness, the refractive index of the film, the refractive index of the substrate, or some combination thereof); multilayer thin films; sharp edges and surface features that diffract or otherwise generate complex interference effects; unresolved surface roughness; unresolved surface features, for example, a sub-wavelength width groove on an otherwise smooth surface; dissimilar materials (for example, the surface may comprise a combination of thin film and a solid metal, in which case the library may include both surface structure types and automatically identify the film or the solid metal by a match to the corresponding frequency-domain spectra); surface structure that give rise to optical activity such as fluorescence; spectroscopic properties of the surface, such as color and wavelength-dependent reflectivity; polarization-dependent properties of the surface; and deflections, vibrations or motions of the surface or deformable surface features that result in perturbations of the interference signal.

In some embodiments, the limited coherence length of the light used to generate the scanning interferometry signal is based on a white light source, or more generally, a broadband light source. In other embodiments, the light source may be monochromatic, and the limited coherence length can result from using a high numerical aperture (NA) for directing light to, and/or receiving light from, the test object. The high NA causes light rays to contact the test surface over a range of angles, and generates different spatial frequency components in the recorded signal as the OPD is scanned. In yet further embodiments, the limited coherence can result from a combination of both effects.

The origin of the limited coherence length is also a physical basis for there being information in the scanning interferometry signal. Specifically, the scanning interferometry signal contains information about complex surface structure because it is produced by light rays contacting the test surface with many different wavelengths and/or at many different angles.

In the processing techniques described herein, information derivable from a scanning interferometry signal for a first surface location of a test object (including the scanning interferometry signal itself) is compared to information corresponding to multiple models of the test object, where the multiple models are parametrized by a series of characteristics for the test object. For example, the test object can be modeled as a thin film and the series of characteristics can be a series of values for the thickness of the thin film. While the information being compared might include, for example, information about the frequency domain phase profile, it might also include information about the shape of the scanning interferometry data and/or information about the frequency domain amplitude profile. Furthermore, to focus the comparison on the complex surface structure, and not the surface height at the first surface location, the multiple models can all correspond to a fixed surface height for the test object at the first surface location. The comparison itself can be based on calculating a merit function indicative of the similarity between the information from the actual scanning interferometry signal and the information from each of the models. For example, the merit function can be indicative of fit between the information derivable from the scanning interferometry data and function parametrized by the series of characteristics.

Furthermore, in some embodiments, the series of characteristics corresponds to a characteristic of the test object at second location different from the first location, including for example, diffractive surface structures that contribute to the interface signal for the first surface locations. Thus, while we often refer to the complex surface structure as being something other than surface height at the first surface location corresponding to the scanning interferometry signal, the complex surface structure may correspond to surface height features spaced from the first surface location corresponding to the scanning interferometry signal.

The methods and techniques described herein can be used for in-process metrology measurements of semiconductor chips. For example, scanning interferometry measurements can be used for non-contact surface topography measurements semiconductor wafers during chemical mechanical polishing (CMP) of a dielectric layer on the wafer. CMP is used to create a smooth surface for the dielectric layer, suitable for precision optical lithography. Based on the results of the interferometric topography methods, the process conditions for CMP (e.g., pad pressure, polishing slurry composition, etc.) can be adjusted to keep surface non-uniformities within acceptable limits.

We now summarize various aspects and features of the invention.

In general, in one aspect, the invention features a method including: comparing information derivable from a scanning interferometry signal for a first surface location of a test object to information corresponding to multiple models of the test object, wherein the multiple models are parametrized by a series of characteristics for the test object.

Embodiments of the invention may incude any of the following features.

The method may further include determining an accurate characteristic for the test object based on the comparison.

The method may further include determining a relative surface height for the first surface location based on the comparison. Furthermore, the determining of the relative surface height may include determining which model corresponds to an accurate one of the characteristic for the test object based on the comparison, and using the model corresponding to the accurate characteristic to calculate the relative surface height.

For example, the using of the model corresponding to the accurate characteristic may include compensating data from the scanning interferometry signal to reduce contributions arising from the accurate characteristic. The compensating of the data may include removing a phase contribution arising from the accurate characteristic from a phase component of a transform of the scanning interferometry signal for the test object, and the using of the model corresponding to the accurate characteristic may further include calculating the relative surface height from the phase component of the transform after the phase contribution arising from the accurate characteristic has been removed.

In another example, using the model corresponding to the accurate characteristic to calculate the relative surface height may include determining a position of a peak in a correlation function used to compare the information for the test object to the information for the model corresponding to the accurate characteristic.

The method may further include comparing information derivable from the scanning interferometry signal for additional surface locations to the information corresponding to the multiple models. Also, the method may further include determining a surface height profile for the test object based on the comparisons.

The comparing may include calculating one or more merit functions indicative of a similarity between the information derivable from the scanning interferometry signal and the information corresponding to each of the models.

The comparing may include fitting the information derivable from the scanning interferometry signal to an expression for the information corresponding to the models.

The information corresponding to the multiple models may include information about at least one amplitude component of a transform (e.g., a Fourier transform) of a scanning interferometry signal corresponding to each of the models of the test object. Likewise, the information derivable from the scanning interferometry signal includes information about at least one amplitude component of a transform of the scanning interferometry signal for the test object.

The comparing may include comparing a relative strength of the at least one amplitude component for the test object to the relative strength of the at least one amplitude component for each of the models.

The information corresponding to the multiple models may be a function of a coordinate for the transform. For example, the information corresponding to the multiple models may include an amplitude profile of the transform for each of the models. Furthemore, the comparing may include comparing an amplitude profile of a transform of the scanning interferometry signal for the test object to each of the amplitude profiles for the models.

The comparing may also include comparing information in a phase profile of the transform of the scanning interferometry signal for the test object to information in a phase profilde of the transform for each of the models. For example, the information in the phase profiles may include information about nonlinearity of the phase profile with respect to the transform coordinate and/or information about a phase gap value.

The information derivable from the scanning interferometry signal and which is being compared may be a number. Alternatively, the information derivable from the scanning interferometry signal and which is being compared may be a function. For example, it may be a function of scan position or a function of spatial frequency.

The information for the test object may be derived from a transform (e.g., a Fourier transform) of the scanning interferometry signal for the test object into a spatial frequency domain. The information for the test object may include information about an amplitude profile of the transform and/or a phase profile of the transform.

The information for the test object may relate to a shape of the scanning interferometry signal for the test object at the first location. For example, the information for the test object may relate to a fringe contrast magnitude in the shape of the scanning interferometry signal. It may also relate to a relative spacings between zero-crossings in the shape of the scanning interferometry signal. It may also be expressed as a function of scan position, wherein the function is derived from the shape of the scanning interferometry signal.

The comparing may include calculating a correlation function (e.g., a complex correlation function) between the information for the test object and the information for each of the models. The comparing may further include determining one or more peak values in each of the correlation functions. The method may then further include determining an accurate characteristic for the test object based on the parameterization of the model corresponding to the largest peak value. Alternately, or in addition, the method may further include determining a relative surface height for the test object at the first surface location based on a coordinate for at least one of the peak values in the correlation functions.

The multiple models may correspond to a fixed surface height for the test object at the first location.

The series of characteristics may include a series of values for at least one physical parameter of the test object. For example, the test object may include a thin film layer having a thickness, and the physical parameter may be the thickness of the thin film at the first location.

The series of characteristics may include a series of characteristics of the test object at a second surface location different from the first surface location. For example, the test object may include structure at the second surface location that diffracts light to contribute to the scanning interferometry signal for the first surface location. In one example, the series of characteristics at the second surface location may include permutations of a magnitude for a step height at the second location and a position for the second location. In another example, the series of characteristics at the second surface location may include permutations of a modulation depth for a grating and an offset position of the grating, wherein the grating extends over the second location.

The series of characteristics may be a series of surface materials for the test object.

The series of characteristics may be a series of surface layer configurations for the test object.

The scanning interferometry signal may be produced by a scanning interferometry system, and the comparing may include accounting for systematic contributions to the scanning interferometry signal arising from the scanning interferometry system. For example, the systematic contributions may include information about a dispersion in a phase change on reflection from components of the scanning interferometry system. Furthermore, the method may also include comparing information derivable from the scanning interferometry signal for additional surface locations to the information corresponding to the multiple models, in which case, the systematic contributions may be resolved for multiple ones of the surface locations. The method may further include calibrating the systematic contributions of the scanning interferometry system using another test object having known properties.

The scanning interferometry signal may produced by imaging test light emerging from the test object to interfere with reference light on a detector, and varying an optical path length difference from a common source to the detector between interfering portions of the test and reference light, wherein the test and reference light are derived from the common source (e.g., a spatially extended source), and wherein the scanning interferometry signal corresponds to an interference intensity measured by the detector as the optical path length difference is varied.

The test and reference light may have a spectral bandwidth greater than about 5% of a central frequency for the test and reference light.

The common source may have a spectral coherence length, and the optical path length difference is varied over a range larger than the spectral coherence length to produce the scanning interferometry signal.

Optics used to direct test light onto the test object and image it to the detector may define a numerical aperture for the test light greater than about 0.8.

The method may further include producing the scanning interferometry signal.

In another aspect, the invention features an apparatus including: a computer readable medium having a program that causes a processor in a computer to compare information derivable from a scanning interferometry signal for a first surface location of a test object to information corresponding to multiple models for the test object, wherein the multiple models are parametrized by a series of characteristics for the test object.

The apparatus may include any of the features described above in connection with the method.

In another aspect, the invention features an apparatus including: a scanning interferometry system configured to produce a scanning interferometry signal; and an electronic processor coupled to the scanning interferometry system to receive the scanning interferometry signal and programmed to compare information derivable from a scanning interferometry signal for a first surface location of a test object to information corresponding to multiple models of the test object, wherein the multiple models are parametrized by a series of characteristics for the test object.

The apparatus may include any of the features described above in connection with the method.

In general, in another aspect, the invention features a method including: chemically mechanically polishing a test object; collecting scanning interferometry data for a surface topography of the test object; and adjusting process conditions for the chemically mechanically polishing of the test object based on information derived from the scanning interferometry data. For example, the process conditions may be pad pressure and/or polishing slurry composition. In preferred embodiments, adjusting the process conditions based on the information derived from the scanning interferometry data may include comparing information derivable from the scanning interferometry signal for at least a first surface location of a test object to information corresponding to multiple models of the test object, wherein the multiple models are parametrized by a series of characteristics for the test object. Analysis of the scanning interferometry signal may further include any of the features described above with the first-mentioned method.

Unless otherwise defined, all technical and scientific terms used herein have the same meaning as commonly understood by one of ordinary skill in the art to which this invention belongs. In case of conflict with publications, patent applications, patents, and other references mentioned incorporated herein by reference, the present specification, including definitions, will control.

Other features, objects, and advantages of the invention will be apparent from the following detailed description.

BRIEF DESCRIPTION OF THE DRAWINGS

Like reference numerals in different drawings refer to common elements.

DETAILED DESCRIPTION

Figure 1:
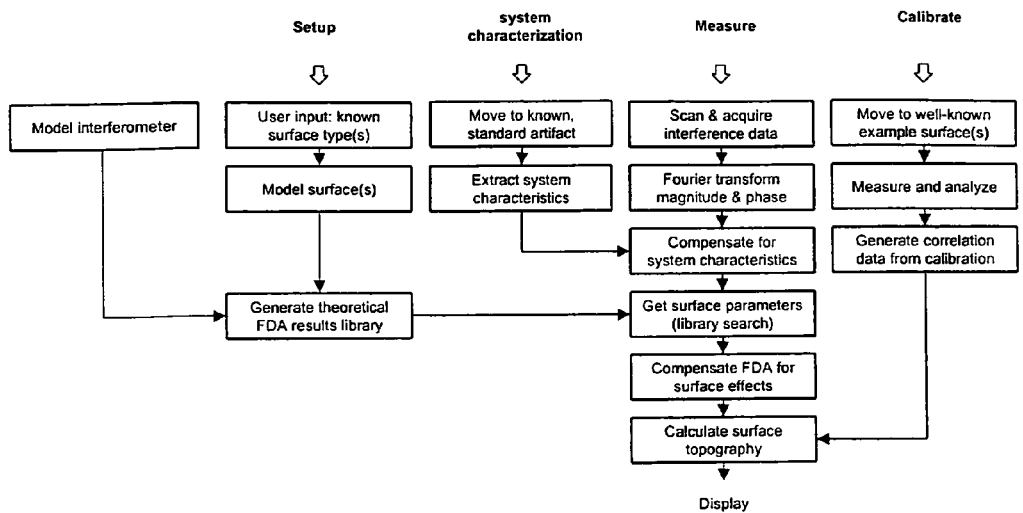
FIG. 1 is a flow chart of an interferometry method.

FIG. 1 shows a flow chart that generally describes one embodiment of the invention in which the analysis of the scanning interferometry data is performed in the spatial frequency domain.

Referring to FIG. 1, to measure data from a test object surface an interferometer is used to mechanically or electro-optically scan the optical path difference (OPD) between a reference and measurement path, the measurement path being directed to an object surface. The OPD at the beginning of the scan is a function of the local height of the object surface. A computer records an interference intensity signal during the OPD scan for each of multiple camera pixels corresponding to different surface locations of the object surface. Next, after storing interference intensity signal as a function of OPD scan position for each of the different surface locations, the computer performs a transform (e.g., a Fourier Transform) to generate a frequency-domain spectrum of the signal. The spectrum contains both magnitude and phase information as a function of the spatial frequency of the signal in the scanning dimension. For example, a suitable frequency domain analysis (FDA) for generating such a spectrum is disclosed in commonly owned U.S. Pat. No. 5,398,113 by Peter de Groot and entitled "Method and Apparatus for Surface Topography Measurements by Spatial-Frequency Analysis of Interferograms," the contents of which are incorporated herein by reference.

In a separate step, the computer generates a library of theoretical predictions for frequency-domain spectra for a variety of surface parameters and a model for the interferometer. These spectra may for example cover a range of possible thin film thicknesses, surface materials, and surface textures. In preferred embodiments, the computer generates library spectra for a constant surface height, e.g. height=zero. Thus, in such embodiments, the library contains no information regarding surface topography, only information relative to the type of surface structure and the interaction of this surface structure, the optical system, the illumination, and detection system when generating distinctive features of the frequency-domain spectra. As an alternative, the prediction library may be generated empirically, using sample artifacts. As another alternative, the library may use information from prior supplemental measurements of the object surface provided by other instruments, for example an ellipsometer, and any other input from a user regarding known properties of the object surface, so as to reduce the number of unknown surface parameters. Any of these techniques for library creation, theoretical modeling, empirical data, or theory augmented by supplemental measurements, may be expanded by interpolation to generate intermediate values, either as part of the library creation or in real time during a library search.

In a next step, the experimental data is compared to the prediction library by means of a library search that provides surface structure parameters. In the example case of a film of unknown thickness, the library for a single surface type, e.g. $SiO_2$ on Si, would range over many possible film thicknesses with the top surface height always equal to zero. Another example case would be surface roughness, for which the adjustable parameter may be roughness depth and/or spatial frequency. The library search leads to a match to those characteristics of the FDA spectra that are independent of surface height, for example, the average value of the magnitude spectrum, which is related to the overall reflectivity of the surface, or the variation in magnitude as a function of spatial frequency, which in a monochromatic high-NA system relates to the scattering angle of the reflected light.

The analysis may also include a system characterization, which includes, e.g. measuring one or more reference artifacts having a known surface structure and surface topography, so as to determine parameters such as system wavefront error, dispersion, and efficiency that may not be included in the theoretical model.

Furthermore, the analysis may include an overall calibration, which includes e.g., measuring one or more reference artifacts to determine the correlation between measured surface parameters, such as film thickness as determined by the library search, and the values for these parameters as determined independently, e.g. by ellipsometric analysis.

Based on the comparison of the experimental data to the prediction library, the computer identifies the surface model corresponding to the best match. It may then displays or transmits surface parameter results numerically or graphically to the user or to a host system for further analysis or for data storage. Using the surface parameter results, the computer may then determine surface height information in addition to characteristics identified by the library search. In some embodiments, the computer generates a compensated phase spectrum, for example by subtracting the corresponding theoretical phase spectrum directly from the experimental phase spectrum. The computer then determines the local surface height for one or more surface points by analysis of the compensated phase as a function of spatial frequency, for example by analysis of the coefficients generated by a linear fit. Thereafter, the computer generates a complete three-dimensional image constructed from the height data and corresponding image plane coordinates, together with graphical or numerical display of the surface characteristics as determined by the library search.

In some cases, the library search and data collection can be performed iteratively to further improve the results. Specifically, the library search can be refined on a pixel-by-pixel or regional basis, by the creation of refined libraries relevant to the local surface type. For example, if it is found that the surface has a thin film of approximately 1 micron during a preliminary library search, then the computer may generate a fine-grain library of example values close to 1 micron to further refine the search.

In further embodiments, the user may only be interested in the surface characteristics modeled by the prediction library, but not surface height, in which case the steps for determining surface height are not performed. Conversely, the user may only be interested in surface height, but not the surface characteristics modeled in the prediction library, in which case the computer uses the comparison between the experimental data and the prediction library to compensate the experimental data for the contributions of the surface characteristics, so that the surface height is more accurately determined, but need not explicitly determine the surface characteristics or display them.

The analysis may be applied to a variety of surface analysis problems, including: simple thin films (in which case, for example, the variable parameter of interest may be the film thickness, the refractive index of the film, the refractive index of the substrate, or some combination thereof); multilayer thin films; sharp edges and surface features that diffract or otherwise generate complex interference effects; unresolved surface roughness; unresolved surface features, for example, a sub-wavelength width groove on an otherwise smooth surface; dissimilar materials (for example, the surface may comprise a combination of thin film and a solid metal, in which case the library may include both surface structure types and automatically identify the film or the solid metal by a match to the corresponding frequency-domain spectra); optical activity such as fluorescence; spectroscopic properties of the surface, such as color and wavelength-dependent reflectivity; polarization-dependent properties of the surface; deflections, vibrations or motions of the surface or deformable surface features that result in perturbations of the interference signal; and data distortions related to the data acquisition procedure, e.g. a data acquisition window that does not fully encompass the interference intensity data.

The interferometer may include any of the following features: a spectrally narrow-band light source with a high numerical aperture (NA) objective; a spectrally broad band light source; a combination of a high NA objective and a spectrally broadband source; an interferometric microscope objectives, including oil/water immersion and solid immersion types, in e.g. Michelson, Mirau or Linnik geometries; a sequence of measurements at multiple wavelengths; unpolarized light; and polarized light, including linear, circular, or structured. For example, structured polarized light may involve, for example, a polarization mask, generating different polarizations for different segments of the illumination or imaging pupils, so as to reveal polarization-dependent optical effects attributable to surface characteristics. The interferometer may also include the overall system calibration, described above.

In comparing the theoretical and experimental data, the library search may be based on any of the following: a product of, or a difference between, magnitude and/or phase data in the frequency spectrum, including, e.g., the product of, or difference between, the average magnitude and the average phase, the average magnitude itself, and the average phase itself; the slope, width and/or height of the magnitude spectrum; interference contrast; data in the frequency spectrum at DC or zero spatial frequency; nonlinearity or shape of the magnitude spectrum; the zero-frequency intercept of the phase; nonlinearity or shape of the phase spectrum; and any combination of these criteria. Note that as used herein magnitude and amplitude are used interchangeably.

Figure 2:
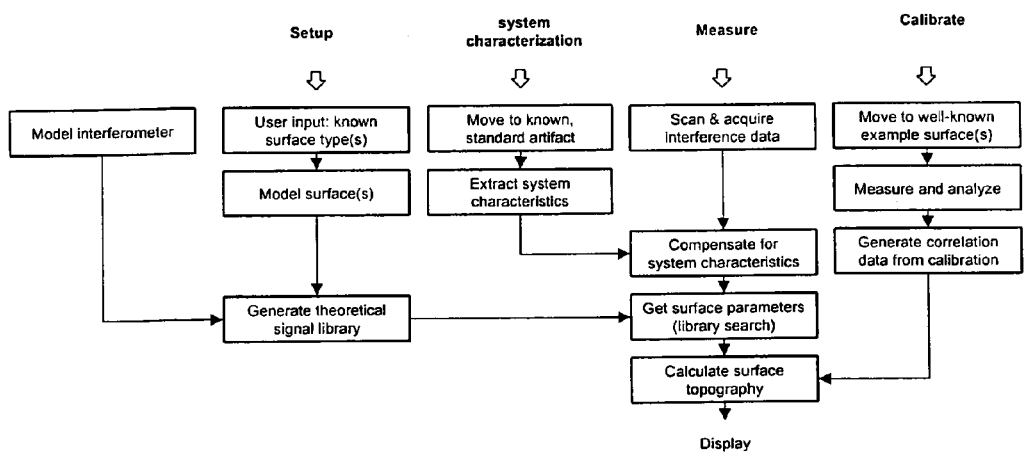
FIG. 2 is a flow chart showing a variation of the interferometry method of FIG. 1.

FIG. 2 shows a flow chart that generally describes another embodiment for the analysis of scanning interferometry data. The analysis is similar to that described for FIG. 1 except that comparison between the experimental data and the prediction library is based on information in scan coordinate domain. The experimentl signal may be characterized by a quasi-periodic carrier oscillation modulated in amplitude by an envelope function with respect to the scan coordinate. In comparing the theoretical and experimental data, the library search may be based on any of the following: average signal strength; the shape of the signal envelope, including e.g. deviation from some ideal or reference shape such as a gaussian; the phase of the carrier signal with respect to the envelope function; the relative spacing of zero crossings and/or signal maxima and minima; values for maxima and minima and their ordering; peak value of the correlation between the library and measured signals, after adjusting for optimal relative scan position; and any combination of these criteria.

In what follows we provide a detailed mathematical description of the analyses and provide examples. First, we describe exemplary scanning interferometers. Second, we determine a mathematical model for scanning interferometry data. Third, we describe optical properties of surfaces and how to use such information to generate accurate models of scanning interferometry data for different surface characteristics. Fourth, we describe how experimental interferometry data can be compared to the prediction library to provide information about the test object. Initially, we will describe thin film applications, and later we will describe applications to other complex surface structures, specifically, optically under-resolved step heights and grating patterns. Also, we will initially focus on analyses in the spatial frequency domain, and later we will describe analyses in the scan coordinate domain.

Figure 3:
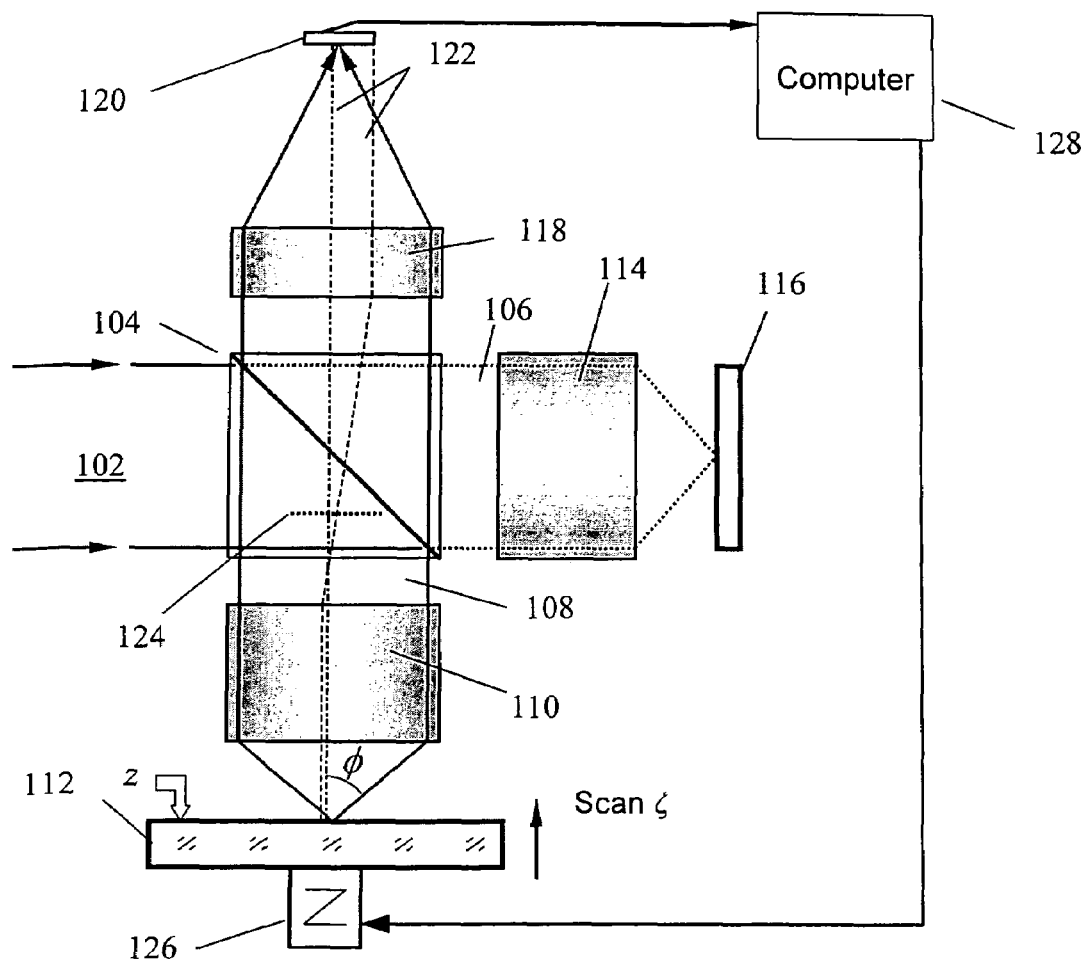
FIG. 3 is a schematic drawing of a Linnik-type scanning interferometer.

FIG. 3 shows a scanning interferometer of the Linnik type. Illumination light 102 from a source (not shown) is partially transmitted by a beam splitter 104 to define reference light 106 and partially reflected by beam splitter 104 to define measurement light 108. The measurement light is focused by a measurement objective 110 onto a test sample 112 (e.g., a sample comprising a thin single- or multi-layer film of one or more dissimilar materials). Similarly, the reference light is focused by a reference objective 114 onto a reference mirror 116. Preferably, the measurement and reference objectives have common optical properties (e.g., matched numerical apertures). Measurement light reflected (or scattered or diffracted) from the test sample 112 propagates back through measurement objective 110, is transmitted by beam splitter 104, and imaged by imaging lens 118 onto a detector 120. Similarly, reference light reflected from reference mirror 116 propagates back through reference objective 114, is reflected by beam splitter 104, and imaged by imaging lens 118 onto a detector 120, where it interferes with the measurement light.

For simplicity, FIG. 3 shows the measurement and reference light focusing onto particular points on the test sample and reference mirror, respectively, and subsequently interfering on a corresponding point on the detector. Such light corresponds to those portions of the illumination light that propagate perpendicular to the pupil planes for the measurement and reference legs of the interferometer. Other portions of the illumination light ultimately illuminate other points on the test sample and reference mirror, which are then imaged onto corresponding points on the detector. In FIG. 3, this is illustrated by the dashed lines 122, which correspond to the chief rays emerging from different points on the test sample that are imaged to corresponding points on the detector. The chief rays intersect in the center of the pupil plane 124 of the measurement leg, which is the back focal plane of measurement objective 110. Light emerging from the test sample at an angle different from that of the chief rays intersect at a different location of pupil plane 124.

In preferred embodiments, detector 120 is a multiple element (i.e., multi-pixel) camera to independently measure the interference between the measurement and reference light corresponding to different points on the test sample and reference mirror (i.e., to provide spatial resolution for the interference pattern).

A scanning stage 126 coupled to test sample 112 scans the position of the test sample relative to measurement objective 110, as denoted by the scan coordinate $\zeta$ in FIG. 3. For example, the scanning stage can be based on a piezoelectric transducer (PZT). Detector 120 measures the intensity of the optical interference at one or more pixels of the detector as the relative position of the test sample is being scanned and sends that information to a computer 128 for analysis.

Because the scanning occurs in a region where the measurement light is being focused onto the test sample, the scan varies the optical path length of the measurement light from the source to the detector differently depending on the angle of the measurement light incident on, and emerging from, the test sample. As a result, the optical path difference (OPD) from the source to the detector between interfering portions of the measurement and reference light scale differently with the scan coordinate $\zeta$ depending on the angle of the measurement light incident on, and emerging from, the test sample. In other embodiments of the invention, the same result can be achieved by scanning the position of reference mirror 116 relative to reference objective 114 (instead of scanning test sample 112 realtive to measurement objective 110).

This difference in how OPD varies with the scan coordinate $\zeta$ introduces a limited coherence length in the interference signal measured at each pixel of the detector. For example, the interference signal (as a function of scan coordinate) is typically modulated by an envelope having a spatial coherence length on the order of $\lambda/2(NA)^2$, where $\lambda$ is the nominal wavelength of the illumination light and NA is the numerical aperture of the measurement and reference objectives. As described further below, the modulation of the interference signal provides angle-dependent information about the reflectivity of the test sample. To increase the limited spatial coherence, the objectives in the scanning interferometer preferably define a large numerical aperture, e.g., greater than about 0.7 (or more preferably, greater than about 0.8, or greater than about 0.9). The interference signal can also be modulated by a limited temporal coherence length associated with the spectral bandwidth of the illumination source. Depending on the configuration of the interferometer, one or the other of these limited coherence length effects may dominate, or they may both contribute substantially to the overall coherence length.

Figure 4:
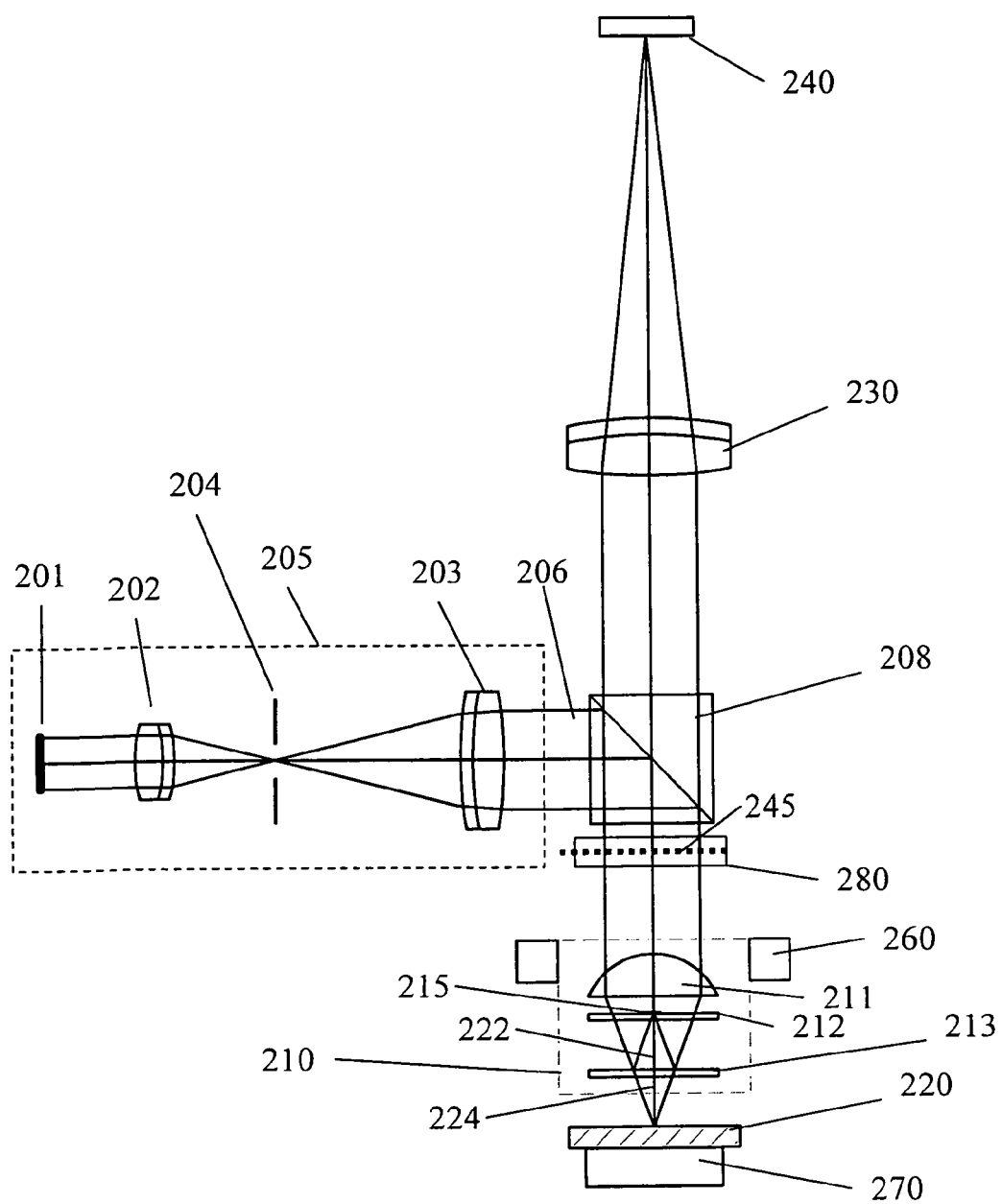
FIG. 4 is a schematic drawing of a Mirau-type scanning interferometer.

Another example of a scanning interferometer is the Mirau-type interferometer shown in FIG. 4.

Referring to FIG. 4, a source module 205 provides illumination light 206 to a beam splitter 208, which directs it to a Mirau interferometric objective assembly 210. Assembly 210 includes an objective lens 211, a reference flat 212 having a reflective coating on a small central portion thereof defining a reference mirror 215, and a beam splitter 213. During operation, objective lens 211 focuses the illumination light towards a test sample 220 through reference flat 212. Beam splitter 213 reflects a first portion of the focusing light to reference mirror 215 to define reference light 222 and transmits a second portion of the focusing light to test sample 220 to define measurement light 224. Then, beam splitter 213 recombines the measurement light reflected (or scattered) from test sample 220 with reference light reflected from reference mirror 215, and objective 211 and imaging lens 230 image the combined light to interfere on detector (e.g., a multi-pixel camera) 240. As in the system of FIG. 3, the measurement signal(s) from the detector is sent to a computer (not shown).

The scanning in the embodiment of FIG. 4 involves a piezoelectric transducer (PZT) 260 coupled to Mirau interferometric objective assembly 210, which is configured to scan assembly 210 as a whole relative to test sample 220 along the optical axis of objective 211 to provide the scanning interferometry data $I(\zeta,h)$ at each pixel of the camera. Alternatively, the PZT may be coupled to the test sample rather than assembly 210 to provide the relative motion there between, as indicated by PZT actuator 270. In yet further embodiments, the scanning may be provided by moving one or both of reference mirror 215 and beam splitter 213 relative to objective 211 along the optical axis of objective 211.

Source module 205 includes a spatially extended source 201, a telescope formed by lenses 202 and 203, and a stop 204 positioned in the front focal plane of lens 202 (which coincides with the back focal plane of lens 203). This arrangement images the spatially extended to source onto the pupil plane 245 of Mirau interferometric objective assembly 210, which is an example of Koehler imaging. The size of stop controls the size of the illumination field on test sample 220. In other embodiments, the source module may include an arrangement in which a spatially extended source is imaged directly onto the test sample, which is known as critical imaging. Either type of source module may be used with the Linnik-type scanning interferometry system of FIG. 1.

In further embodiments of the invention, the scanning interferometry system may used to determine angle-dependent scattering or diffraction information about a test sample, i.e., for scatterometry. For example, the scanning interferometry system may be used to illuminate a test sample with test incident over only a very narrow range of incident angles (e.g., substantially normal incidence or otherwise collimated), which may then be scattered or diffracted by the test sample. The light emerging from the sample is imaged to a camera to interfere with reference light as described above. The spatial frequency of each component in the scanning interferometry signal will depend vary with angle of the test light emerging from the test sample. Thus, a vertical scan (i.e., a scan along the optical axis of an objective) followed by Fourier analysis allows for a measurement of diffracted and/or scattered light as a function of emerging angle, without directly accessing or imaging the back focal plane of the objective. To provide the substantially normal incidence illumination, for example, the source module can be configured to image a point source onto the pupil plane or to otherwise decrease the degree to which the illumination light fills the numerical aperature of the measurement objective. The scatterometry technique may be useful for resolving discrete structures in the sample surface, such as grating lines, edges, or general surface roughness, which may diffract and/or scatter light to higher angles.

In much of the analysis herein, it is assumed that the polarization state of the light in the pupil plane is random, i.e., comprised of approximately equal amounts of both s polarizations (orthogonal to the plane of incidence) and p (orthogonal to the plane of incidence) polarizations. Alternative polarizations are possible, including pure s polarization, such as may be realized by means of a radial polarizer placed in the pupil plane (e.g., in the back-focal plane of the measurement object in the case of a Linnik interferometer and in the back focal plane of the common objective in the Mirau interferometer). Other possible polarizations include radial p polarization, circular polarization, and modulated (e.g. two states, one following the other) polarization for ellipsometric measurements. In other words, optical properties of the test sample can be resolved not only with respect to their angle- or wavelength-dependence, but also with respect to their polarization dependence or with respect to a selected polarization. Such information may also be used to improve the accuracy of thin film structure characterization.

To provide such ellipsometry measurements, the scanning interferometry system may include a fixed or variable polarizer in the pupil plane. Referring again to FIG. 4, the Mirau-type interferometry system, for example, includes polarization optics 280 in the pupil plane to select a desired polarization for the ligh incident on, and emerging from the test sample. Furthermore, the polarization optics may be reconfigurable to vary the selected polarization. The polarization optics may include one or more elements including polarizers, waveplates, apodization apertures, and/or modulation elements for selecting a given polarization. Furthermore, the polarization optics may be fixed, structured or reconfigurable, for the purpose of generating data similar to that of an ellipsometer. For example, a first measurement with a radially-polarized pupil for s polarization, followed by a radially-polarized pupil for p polarization. In another example, one may use an apodized pupil plane with linearly polarized light, e.g., a slit or wedge, which can be rotated in the pupil plane so as to direct any desired linear polarization state to the object, or a reconfigurable screen such as a liquid crystal display.

Moreover, the polarization optics may provide a variable polarization across the pupil plane (e.g., by including multiple polarizers or a spatial modulator). Thus, one can "tag" the polarization state according to spatial frequency, for example, by providing a different polarization for high angles of incidence than shallow angles.

In yet further embodiments, the selectable polarization may be combined with a phase shift as a function of polarization. For example, the polarization optics may include a linear polarizer is positioned in the pupil plane and followed by two waveplates (e.g., eighth-wave plates) in opposing quadrants of the pupil plane. The linear polarization results in a full range of polarization angles with respect to the incident planes of the objective. If the waveplates are aligned so that, for example, the predominately s-polarized light has a fixed phase shift, then both radial s polarized and p polarized light are present simultaneously, but shifted in phase with respect to each other, e.g., by pi, so that the interferometer is effectively detecting the difference between these two polarization states as the fundamental signal.

In further embodiments, polarization optics may be positioned elsewhere in the apparatus. For example, linear polarization can be achieved anywhere in the system.

We now describe a physical model for the scanning interferometry signal.

The object surface has height features h which we wish to profile over an area indexed by lateral coordinates x,y. The stage provides a smooth, continuous scan $\zeta$ either of the interference objective or, as shown, of the object itself. During the scan, a computer records intensity data $I_{\zeta,h}$ for each image point or camera pixel in successive camera frames. Note that the key dependencies of the intensity $I_{\zeta,h}$ on the scan position and surface height are indicated by subscripts—a notation that we shall employ throughout.

Figure 5:
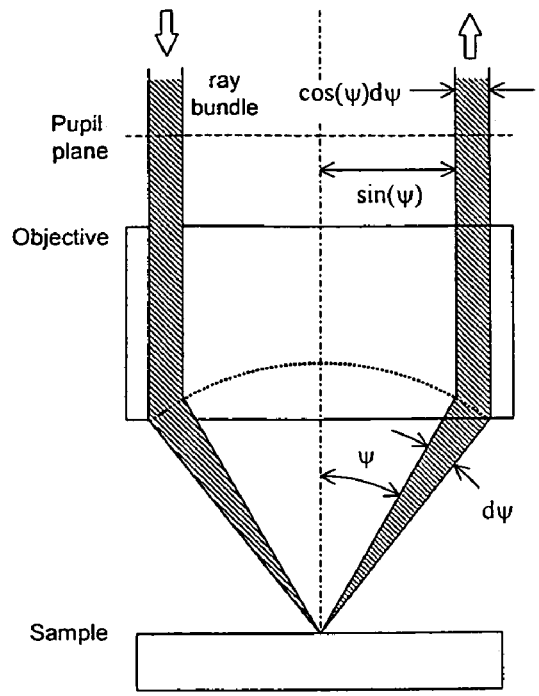
FIG. 5 is a diagram showing illumination of the test sample through an objective lens.

A proper physical model of the optics can be very elaborate, taking into account the partial coherence of the light source, polarization mixing in the interferometer, the imaging properties of high-NA objectives, and the interaction of electric field vectors at high angles of incidence and in the presence of discontinuous surface features. For convenience, we simplify the model by assuming random polarization and diffuse, low-coherence extended sources. Modeling the interference signal simplifies to adding up the contributions of all of the ray bundles passing through the pupil plane of the objective and reflecting from the object surface at an incident angle $\psi$, as shown in FIG. 5.

The interference contribution for a single ray bundle through the optical system is proportional to $$g_{\beta,k,\zeta,h} = R_{\beta,k} + Z_{\beta,k} + 2\sqrt{R_{\beta,k}Z_{\beta,k}}\cos[2\beta k n_O(h-\zeta) + (\nu_{\beta,k} - \omega_{\beta,k})] \quad (1)$$

Where $Z_{\beta,k}$ is the effective object intensity reflectivity, including e.g. the effects of the beamsplitter, and $R_{\beta,k}$ is the effective reference reflectivity, including both the beamsplitter and the reference mirror. The index of the ambient medium is $n_O$, the directional cosine for an incident angle $\psi$ is $$\beta = \cos(\psi) \quad (2)$$

and the wavenumber for the source illumination is $$k = (2\pi/\lambda) \quad (3)$$

The sign convention for the phase causes an increase in surface height to correspond to a positive change in phase. The phase term has a contribution $\omega_{\beta,k}$ for the object path in the interferometer, including thin film effects from the object surface, and a contribution $\upsilon_{\beta,k}$ for the reference path, including the reference mirror and other optics in the objective.

The total interference signal integrated over the pupil plane is proportional to $$I_{\zeta,h} = \int_0^\infty \int_0^1 g_{\beta,k,\zeta,h} U_\beta V_k \beta \, d\beta \, dk \quad (4)$$

where $U_\beta$ is the pupil plane light distribution and $V_k$ the optical spectrum distribution. The weighting factor $\beta$ in Eq. (4) follows from a $\cos(\psi)$ term attributable to the projection angle and a $\sin(\psi)$ term for the diameter of the annulus of width $d\psi$ in the pupil plane:

$$\cos(\psi)\sin(\psi)d\psi = -\beta d\beta \quad (5)$$

Here we assume that the objective obeys the Abbé sine condition as shown in FIG. 5. This relatively simple weighting is possible for randomly polarized, spatially incoherent illumination, for which all ray bundles are independent from each other. Finally, the integration limits over all incident angles implies $0 \leq \beta \leq 1$ and the spectrum integration over all wavenumbers $0 \leq k \leq \infty$.

In a frequency domain analysis (FDA), we first calculate the Fourier Transform of the interference intensity signal $I_{\zeta,h}$. For the literal (non-numerical) analysis we shall use the un-normalized Fourier integral $$q_{K,h} = \int_{-\infty}^{\infty} I_{\zeta,h} \exp(iK\zeta) \, d\zeta \quad (6)$$

where K is the spatial frequency, e.g. in cycles per µm. The frequency-domain value $q_{K,h}$ carries units of inverse wavenumber, e.g. µm. From this there follows a power spectrum $$Q_{K,h} = |q_{K,h}|^2 \quad (7)$$

and a phase spectrum $$\phi''_{K,h} = \arg(q_{K,h}). \quad (8)$$

The double prime for $\phi''_{K,h}$ means that there is a two-fold uncertainty in the fringe order, both from pixel to pixel and overall with respect to the starting point in the scan. Conventional FDA then proceeds directly to a determination of surface topography by a linear fit to the phase spectrum $\phi''_{K,h}$ weighted by the power spectrum $Q_{K,h}$. The fit provides for each pixel a slope $$\sigma_h \approx d\phi''/dK \quad (9)$$

and an intercept $$A'' \approx \phi''_{K=0,h}. \quad (10)$$

Note that the intercept or "phase gap" $A''$ is independent of height h, but carries the double prime inherited from the fringe order uncertainty in the phase data. The slope $\sigma$ is free of this uncertainty. From the intercept $A''$ and the slope $\sigma_h$, we can define for a specific mean or nominal spatial frequency K0 a "coherence profile"

$$\Theta_h = \sigma_h K0 \quad (11)$$

and a "phase profile"

$$\theta''_h = \Theta_h + A''. \quad (12)$$

For the simple, idealized case of a perfectly uniform, homogeneous dielectric surface free of thin films and dissimilar material effects, and an optical system perfectly balanced for dispersion, the phase and coherence profiles are linearly proportional to surface height:

$$h_\Theta = \Theta_h/K0 \quad (13)$$

$$h''_\theta = \theta''_h/K0 \quad (14)$$

Of the two height calculations, the height value $h''_\theta$ based on phase is the more accurate, but it has the uncertainty in the fringe order characteristic of monochromatic interferometry. For high resolution, we can use the unambiguous but less precise height value $h_\Theta$ based on coherence to remove this uncertainty and yield a final value $h_\theta$.

Conventional FDA assumes that even for less idealized situations, the interference phase $\phi''_{K,h}$ is still nearly a linear function of spatial frequency. For the present embodiment, however, we determine key parameters of the surface structure such as film thickness by comparing experimental data to a theoretical prediction that may include highly nonlinear phase spectra and associated modulations of the power spectrum.

To this end, we combine the definition of the Fourier Transform Eq. (6) with the interference signal Eq. (4) into the following formula for the predicted FDA spectrum:

$$q_{K,h} = \int_{-\infty}^{\infty} \int_0^{\infty} \int_0^1 g_{\beta,k,\zeta,h} \exp(iK\zeta) U_\beta V_k \beta \, d\beta \, dk \, d\zeta \quad (15)$$

To improve computational efficiency, a partial literal evaluation of the triple integration in Eq. (15) can be performed.

The literal analysis of Eq. (15) begins with a change of the order of integration to first evaluate the individual interference signals $g_{\beta,k,\zeta,h}$ over all scan positions $\zeta$ at fixed $\beta$ and $k$:

$$q_{K,h} = \int_0^{\infty} \int_0^1 U_\beta V_k \beta \left\{ \int_{-\infty}^{\infty} g_{\beta,k,\zeta,h} \exp(iK\zeta) \, d\zeta \right\} d\beta \, dk. \quad (16)$$

After expansion of the cosine term in $g_{\beta,k,\zeta,h}$ in the usual way using $$2 \cos(u) = \exp(iu) + \exp(-iu), \quad (17)$$

the inner integral over $\zeta$ evaluates to $$\int_{-\infty}^{\infty} g_{\beta,k,\zeta,h} \exp(iK\zeta) \, d\zeta = \delta_K (R_{\beta,k} + Z_{\beta,k}) \ldots + \quad (18)$$
$$\delta_{(K-2\beta k n_0)} \sqrt{R_{\beta,k} Z_{\beta,k}} \; \exp[i 2\beta k n_0 h +$$
$$i(\upsilon_{\beta,k} - \omega_{\beta,k})] \ldots +$$
$$\delta_{(K+2\beta k n_0)} \sqrt{R_{\beta,k} Z_{\beta,k}} \; \exp[-i 2\beta k n_0 h -$$
$$i(\upsilon_{\beta,k} - \omega_{\beta,k})]$$

where we have used $$\delta_K = \int_{-\infty}^{\infty} \exp(iK\zeta) \, d\zeta \quad (19)$$

$$\delta_{(K \pm 2\beta k n_0)} = \int_{-\infty}^{\infty} \exp(iK\zeta) \exp(\pm i 2\beta k n_0 \zeta) \, d\zeta. \quad (20)$$

The $\delta$ function carries with it the inverse physical units of the argument, in this case, an inverse wavenumber.

These delta functions validate an equivalency between the spatial frequency K and the product $2\beta k n_0$. A logical change of variables for the next integration is therefore $$\beta = \hat{\kappa}/2kn_0 \quad (21)$$

$$d\beta = d\hat{\kappa}/2kn_0 \quad (22)$$

where $\hat{\kappa}$ has the same meaning as the spatial frequency K, but will be used as a free integration variable. Eq. (18) can be written $$q_{K,h} = \int_0^{\infty} \int_0^{2kn_0} \delta_K (R_{\hat{\kappa},k} + Z_{\hat{\kappa},k}) \Gamma_{\hat{\kappa},k} \, d\hat{\kappa} \, dk \ldots + \quad (23)$$
$$\int_0^{\infty} \int_0^{2kn_0} \delta_{(K-\hat{\kappa})} \sqrt{R_{\hat{\kappa},k} Z_{\hat{\kappa},k}} \; \exp[i\hat{\kappa}h +$$
$$i(\upsilon_{\hat{\kappa},k} - \omega_{\hat{\kappa},k})] \Gamma_{\hat{\kappa},k} \, d\hat{\kappa} \, dk \ldots +$$
$$\int_0^{\infty} \int_0^{2kn_0} \delta_{(K+\hat{\kappa})} \sqrt{R_{\hat{\kappa},k} Z_{\hat{\kappa},k}} \; \exp[-i\hat{\kappa}h -$$
$$i(\upsilon_{\hat{\kappa},k} - \omega_{\hat{\kappa},k})] \Gamma_{\hat{\kappa},k} \, d\hat{\kappa} \, dk$$

where $$\Gamma_{\hat{\kappa},k} = \frac{U_{\hat{\kappa},k} V_k \hat{\kappa}}{4k^2 n_0^2}. \quad (24)$$

Note that by virtue of the change in variables, the $\beta$-dependence for the R, Z, $\upsilon$, $\omega$ terms in Eq. (23) becomes a dependence upon $\hat{\kappa}$ and k.

For the next step, we first note that $$\int_0^{2kn_0} \delta_K f_{\hat{\kappa},k} \, d\hat{\kappa} = \delta_K \int_0^{\infty} H_{(2kn_0 - \hat{\kappa})} f_{\hat{\kappa},k} \, d\hat{\kappa} \quad (25)$$

$$\int_0^{2kn_0} \delta_{(K-\hat{\kappa})} f_{\hat{\kappa},k} \, d\hat{\kappa} = f_{K,k} H_K H_{(2kn_0 - K)} \quad (26)$$

$$\int_0^{2kn_0} \delta_{(K+\hat{\kappa})} f_{\hat{\kappa},k} \, d\hat{\kappa} = f_{-K,k} H_{-K} H_{(2kn_0 + K)} \quad (27)$$

where H is the unitless Heaviside step function defined by $$H_u = \begin{cases} 0 & \text{for } u < 0 \\ 1 & \text{otherwise} \end{cases} \quad (28)$$

and $f$ is an arbitrary function of K and k. Using Eqs. (25) through (27), Eq. (23) becomes $$q_{K,h} = \delta_K \int_0^{\infty} \int_0^{\infty} H_{(2kn_0 - \hat{\kappa})} (R_{\hat{\kappa},k} + Z_{\hat{\kappa},k}) \Gamma_{\hat{\kappa},k} \, d\hat{\kappa} \, dk \ldots + \quad (29)$$
$$\int_0^{\infty} H_K H_{(2kn_0 - K)} \sqrt{R_{K,k} Z_{K,k}} \; \exp[iKh +$$
$$i(\upsilon_{K,k} - \omega_{K,k})] \Gamma_{K,k} \, dk \ldots +$$
$$\int_0^{\infty} H_{-K} H_{(2kn_0 + K)} \sqrt{R_{-K,k} Z_{-K,k}} \; \exp[iKh -$$
$$i(\upsilon_{K,k} - \omega_{-K,k})] \Gamma_{-K,k} \, dk$$

Now using $$\int_0^{\infty} \int_0^{\infty} H_{(2kn_0 - \hat{\kappa})} f_{\hat{\kappa},k} \, d\hat{\kappa} \, dk = \int_0^{\infty} \int_0^{\infty} H_{(2kn_0 - \hat{\kappa})} f_{\hat{\kappa},k} \, dk \, d\hat{\kappa} \quad (30)$$

-continued $$\int_0^\infty H_K H_{(2kn_0-K)} f_{K,k} dk = H_K \int_{K/2n_0}^\infty f_{K,k} dk \qquad (31)$$

$$\int_0^\infty H_{-K} H_{(2kn_0+K)} f_{-K,k} dk = H_{-K} \int_{-K/2n_0}^\infty f_{-K,k} dk \qquad (32)$$

we have the final result $$q_{K,h} = \delta_K \int_{k=0}^\infty \int_{\hat{k}/2n_0}^\infty (R_{K,k} + Z_{K,k}) \Gamma_{\hat{k},k} dk d\hat{k} + \qquad (33)$$

$$H_K \exp(iKh) \int_{K/2n_0}^\infty \sqrt{R_{K,k} Z_{K,k}} \exp[i(\upsilon_{K,k} - \omega_{K,k})] \Gamma_{K,k} dk \ldots +$$

$$H_{-K} \exp(iKh) \int_{-K/2n_0}^\infty \sqrt{R_{-K,k} Z_{-K,k}} \exp[-i(\upsilon_{K,k} - \omega_{-K,k})]$$

$$\Gamma_{-K,k} dk$$

Because there are fewer integrations, Eq. (33) is significantly more efficient computationally that the original triple integral of (15).

Some limit cases are interesting to solve analytically. For example, if the phase contribution $(\upsilon_{K,k} - \omega_{K,k}) = 0$ and the reflectivities R, Z are independent of incident angle and wavelength, then Eq. (33) simplifies to $$q_{K,h} = \delta_K(R+Z) \int_0^\infty \int_{\hat{k}/2n_0}^\infty \Gamma_{\hat{k},k} dk d\hat{k} + H_K \exp(iKh) \sqrt{RZ} \qquad (34)$$

$$\int_{K/2n_0}^\infty \Gamma_{K,k} dk + H_{-K} \exp(iKh) \sqrt{RZ} \int_{-K/2n_0}^\infty \Gamma_{-K,k} dk$$

and we have only to handle integrals involving the weighting factor $\Gamma_{K,k}$ defined in Eq. (24). This idealized case simplifies evaluation of two further limit cases for Eq. (34): Near-monochromatic illumination with a high-NA objective, and broadband illumination with low-NA.

For the case of a near-monochromatic light source having a narrow spectral bandwidth $k_\Delta$, we have the normalized spectrum $$V_k = \frac{1}{k_\Delta} H_{(k-k0)} H_{(k0+k_\Delta-k)} \qquad (35)$$

where k0 is the nominal source wavenumber. The integrations in Eq. (34) are now of the form:

$$\int_0^\infty \int_{K/2n_0}^\infty \Gamma_{\hat{k},k} dk d\hat{k} = \frac{1}{4n_0^2 k_\Delta} \int_0^\infty H_{(k0-\hat{k}/2n_0)} \hat{k} \int_{k0}^{k0+k_\Delta} \frac{U_{\hat{k},k}}{k^2} dk d\hat{k} \qquad (36)$$

$$\int_{K/2n_0}^\infty \Gamma_{K,k} dk = \frac{1}{4n_0^2 k_\Delta} H_{(k0-K/2n_0)} K \int_{k0}^{k0+k_\Delta} \frac{U_{K,k}}{k^2} dk. \qquad (37)$$

Assuming that $U_{K,k}$ is essentially constant over the small bandwidth $k_\Delta$, we have $$\int_0^\infty \int_{K/2n_0}^\infty \Gamma_{\hat{k},k} dk d\hat{k} = \int_0^\infty H_{(k0-\hat{k}/2n_0)} U_{\hat{k},k0} \frac{\hat{k}}{4n_0^2 k0^2} d\hat{k} \qquad (38)$$

$$\int_{K/2n_0}^\infty \Gamma_{K,k} dk = H_{(k0-K/2n_0)} U_{K,k0} \frac{K}{4n_0^2 k0^2}. \qquad (39)$$

where in the evaluation of the integrals we have used $$\frac{-1}{k0+k_\Delta} + \frac{1}{k0} \approx \frac{k_\Delta}{k0}, \qquad (40)$$

valid for a narrow bandwidth $k_\Delta \square k0$. In particular, the positive, nonzero portion of the spectrum reduces to $$q_{K>0,h} = \frac{H_K H_{(k0-K/2n_0)} U_{K,2n_0 k0} K \sqrt{RZ}}{4n_0^2 k0^2} \exp(iKh) \qquad (41)$$

Consequently, for this special case of a narrow spectral bandwidth light source, constant reflectivities R, Z and no phase contributions $\bar{\omega}$, $$\phi''_{K,h} = Kh. \qquad (42)$$

In this special case, the phase is linearly proportional to surface height, consistent with conventional FDA. The spatial frequency also has a direct correspondence to the directional cosine:

$$K = \beta 2 n_0 k0. \qquad (43)$$

Thus there is a one-to-one relationship between the spatial frequency coordinate of the FDA spectra and the angle of incidence. Note further the K weighting in the Fourier magnitude $\sqrt{Q_K}$ calculated from Eq. (41). This is evident in the example spectrum FIG. 6(a), which shows the theoretical prediction for a perfectly uniform filling of the pupil plane over a range starting from normal incidence up to the directional cosine limit imposed by the objective NA:

$$\beta_{NA} = \sqrt{1 - NA^2} \qquad (44)$$

As a second example, consider the case of broadband illumination with uniform illumination restricted to a narrow range $\beta_\Delta$ of directional cosines near normal incidence. The normalize pupil plane distribution is then $$U_\beta = \frac{1}{\beta_\Delta} H_{1-\beta} H_{\beta-(1-\beta_\Delta)}. \qquad (45)$$

After the change of variables, $$U_{K,k} = \frac{1}{\beta_\Delta} H_{(2kn_0-K)} H_{[K-2kn_0(1-\beta_\Delta)]} \qquad (46)$$

The definite integrals in Eq. (34) are in this case of the form $$\int_0^\infty \int_{K/2n_0}^\infty \Gamma_{\hat{\kappa},k} dk d\hat{\kappa} = \frac{1}{\beta_\Delta} \int_0^\infty \int_{\hat{\kappa}/2n_0}^{\hat{\kappa}/(1-\beta_\Delta)2n_0} \frac{V_k \hat{\kappa}}{4k^2 n_0^2} dk d\hat{\kappa} \quad (47)$$

$$\int_{K/2n_0}^\infty \Gamma_{K,k} dk = \frac{1}{\beta_\Delta} \int_{K/2n_0}^{K/(1-\beta_\Delta)2n_0} \frac{V_k K}{4k^2 n_0^2} dk \quad (48)$$

which evaluate to $$\int_0^\infty \int_{K/2n_0}^\infty \Gamma_{\hat{\kappa},k} dk d\hat{\kappa} = \int_0^\infty \frac{V_{\hat{\kappa}/2n_0}}{2n_0} d\hat{\kappa} \quad (49)$$

$$\int_{K/2n_0}^\infty \Gamma_{K,k} dk = \frac{V_{K/2n_0}}{2n_0}. \quad (50)$$

where we have used $$\frac{(1-\beta_\Delta)2n_0}{\hat{\kappa}} - \frac{2n_0}{\hat{\kappa}} = -\frac{2n_0 \beta_\Delta}{\hat{\kappa}} \quad (51)$$

The positive, nonzero portion of the spectrum is for this broadband source illumination and near-normal incidence is therefore $$q_{K>0,h} = \frac{V_{K/2n_0} \sqrt{RZ}}{2n_0} \exp(iKh) \quad (52)$$

Figure 6:
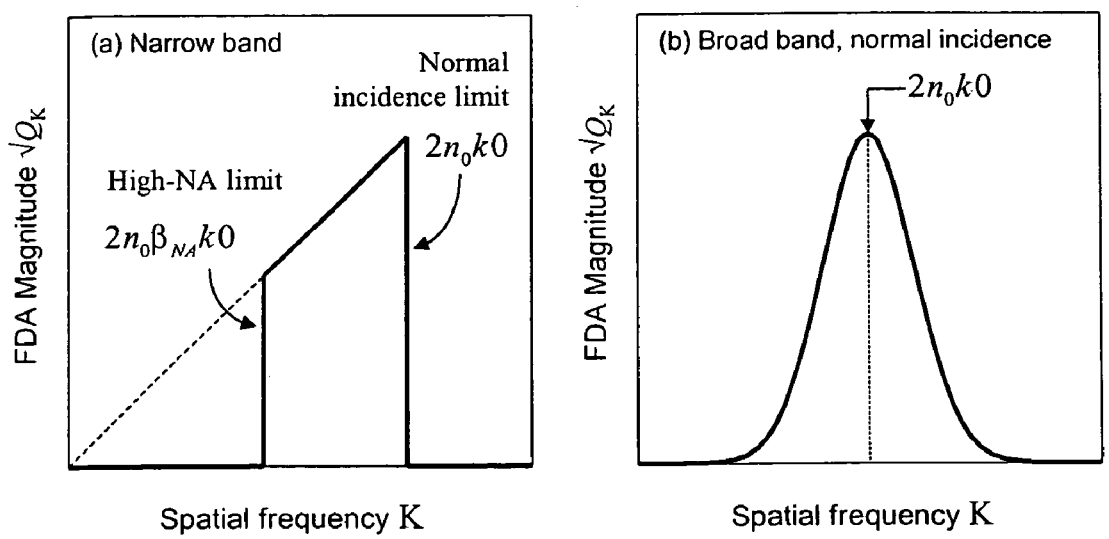
FIG. 6 shows theoretical Fourier amplitude spectra for scanning interferometry data in two limits.

This corresponds closely to the familiar result that the Fourier magnitude $\sqrt{Q_K}$ is proportional to the source spectrum distribution $V_{K/2n_0}$, as shown e.g. in FIG. 6(b) for a gaussian spectrum centered on a nominal or mean wavelength k0. Note that Eq. (52) also conforms to the assumption of linear phase evolution $$\phi''_{K,h} = Kh \quad (53)$$

consistent with conventional FDA.

Since the Fourier magnitude $\sqrt{Q_{K,h}} = |q_{K,h}|$ and phase $\phi''_{K,h} = \arg(q_{K,h})$ are derived from the Fourier Transform of the interference intensity $I_{\zeta,h}$, the inverse transform puts us back into the domain of real interference signals $$I_{\zeta,h} = \int_{-\infty}^\infty q_{\hat{\kappa},h} \exp(-i\hat{\kappa}\zeta) d\hat{\kappa} \quad (54)$$

where once again we have used $\hat{\kappa}$ as for the spatial frequency to emphasize that it is a free variable of integration in Eq. (54). Thus one way to calculate the intensity signal is to generate the Fourier components $q_{K,h}$ by Eq. (33) and transform to $I_{\zeta,h}$ using Eq. (54).

We assume random polarization of the source light in the present model. This does not mean, however, that we should neglect polarization effects. Rather, in the above calculations, we assume an incoherent superposition of equally weighted results from the two orthogonal polarization states s and p defined by the plane of incidence of the illumination. Using superscript notation for the polarizations, $$q_{\beta,k} = q_{\beta,k}^s + q_{\beta,k}^p. \quad (55)$$

Therefore, the average phase angle for unpolarized light at this $\beta$, k would be $$\langle \phi''_{\beta,k} \rangle = \arg(q_{\beta,k}^s + q_{\beta,k}^p). \quad (56)$$

Note that unless the magnitudes are identical for the two polarization contributions, most often $$\langle \phi''_{\beta,k} \rangle \neq (\phi''^{s}_{\beta,k} + \phi''^{p}_{\beta,k})/2. \quad (57)$$

Also, unless $q_{\beta,k}^s$ and $q_{\beta,k}^p$ are perfectly parallel in the complex plane, $$\langle Q_{\beta,k} \rangle \neq (Q_{\beta,k}^s + Q_{\beta,k}^p)/2. \quad (58)$$

The same observation applies to the system and object reflectivities $R_{\beta,k}^s$, $R_{\beta,k}^p$ and $Z_{\beta,k}^s$, $Z_{\beta,k}^p$, respectively; they cannot be summed directly unless they have identical phases.

Provided that we take proper care of the polarization effects in the calculation of the object surface reflectivity, the modeling remains fairly straightforward and is flexible enough to handle the more interesting cases of polarized light further down the line.

The next step is to translate to discrete numerical formulas, in view of a software development. We redefine the relationship between the interference signal $I_{\zeta,h}$ and the Fourier spectrum $q_{K,h}$ using discrete Fourier transforms as $$q_{K,h} = \frac{1}{\sqrt{N}} \sum_\zeta I_{\zeta,h} \exp(iK\zeta) \quad (59)$$

$$I_{\zeta,h} = \frac{1}{\sqrt{N}} \left[ q_0 + \sum_{K>0} q_{K,h} \exp(-iK\zeta) + \sum_{K>0} \bar{q}_{K,h} \exp(iK\zeta) \right] \quad (60)$$

where $\bar{q}_{K,h}$ is the complex conjugate of $q_{K,h}$ and there are N discrete samples in the interference signal $I_{\zeta,h}$. In Eq. (60) and what follows, we have set aside the use of a free variable $\hat{\kappa}$ that was important in the derivations but it is no longer needed as a substitute for the spatial frequency K. The predicted positive-frequency FDA complex spectrum is then $$q_{K\geq 0,h} = \rho_{K\geq 0} \exp(iKh) \quad (61)$$

where the normalized, height-independent coefficients are $$\rho_{K>0} = \frac{\sqrt{N}}{\Upsilon} \sum_k H_{k-K/2n_0} \sqrt{R_{K,k} Z_{K,k}} \exp[i(\upsilon_{K,k} - \omega_{K,k})] \Gamma_{K,k} \quad (62)$$

$$\rho_0 = \frac{\sqrt{N}}{\Upsilon} \sum_{K\geq 0} \sum_k H_{k-K/2n_0} (R_{K,k} + Z_{K,k}) \Gamma_{K,k} \quad (63)$$

where the normalization for the range of integration is $$\Upsilon = \sum_{K\geq 0} \sum_k H_{k-K/2n_0} \Gamma_{K,k} \quad (64)$$

The Heaviside step functions H in Eq. (62) prevent unnecessary contributions to the sums. The weighting factor $\Gamma_{K,k}$ is as defined in Eq. (24).

To compare experiment with theory, we use Eq. (61) to generate an experimental FDA spectrum and Eq. (62) to transform back into the space domain for the theoretical prediction of $I_{\zeta,h}$. This is most efficiently performed by fast Fourier transforms (FFT). The properties of the FFT determine the range of K values. If the N discrete samples for $I_{\zeta,h}$ are spaced by an increment $\zeta_{step}$, there will be N/2+1 positive spatial frequencies starting from zero and rising to N/2 cycles per data trace, spaced by an increment $$K_{step} = \frac{2\pi}{N\zeta_{step}}. \tag{65}$$

To facilitate phase unwrapping in the frequency domain, we try to adjust the zero position for the scan so that it is near the signal peak, thus reducing the phase slope in the frequency domain. Because an FFT always assumes that the first data point in the scan is at zero, the signal should be properly offset.

We now focusing on modeling a sample surface with a thin film.

Figure 7:
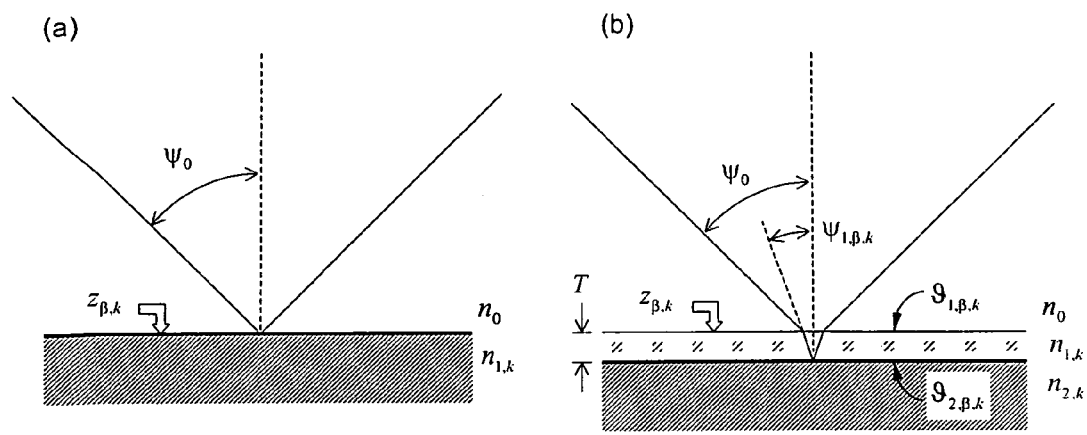
FIG. 7 shows two surface types, with and without a thin film
Figure 8:
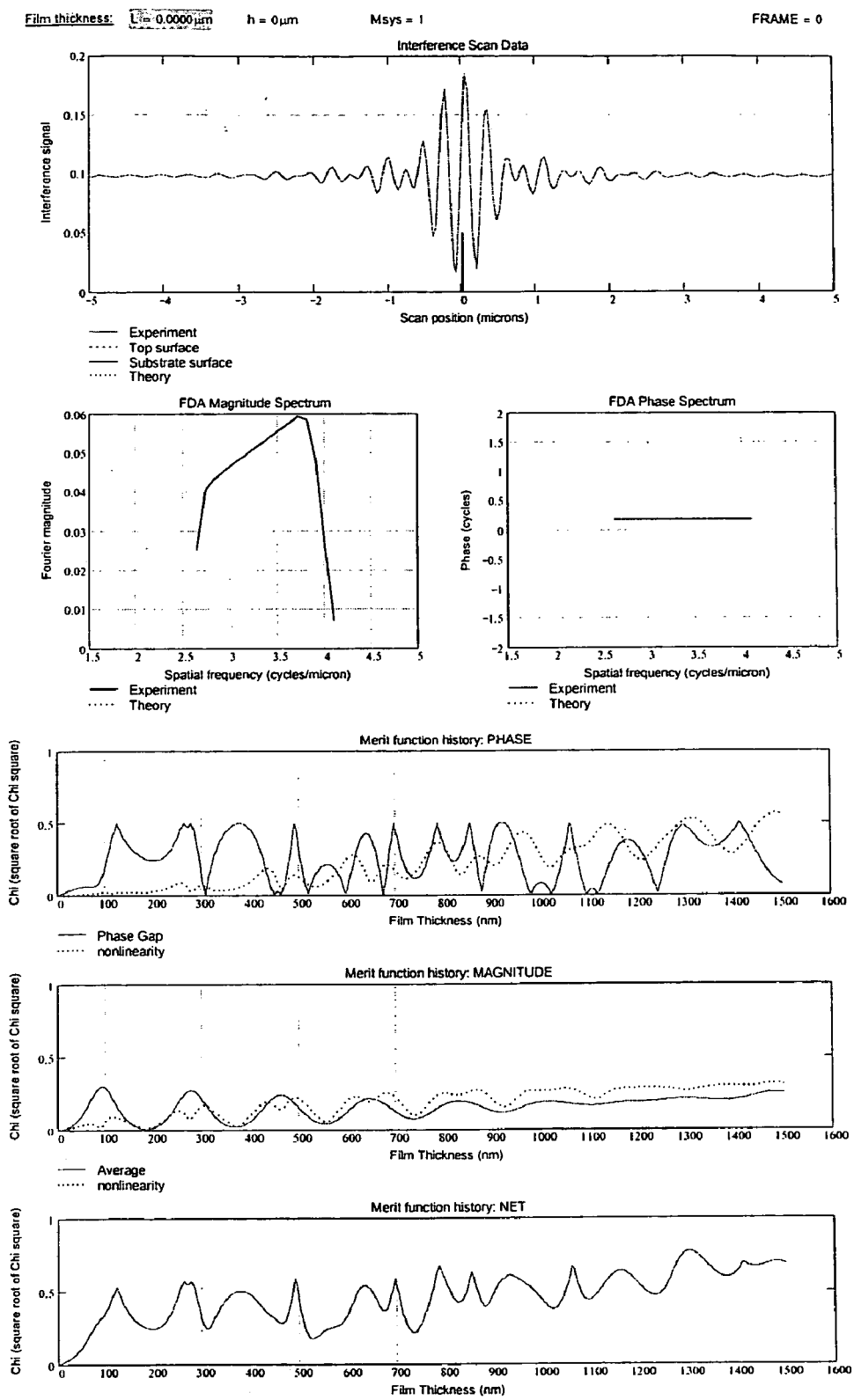
FIG. 8 shows the merit function search procedure for simulation of a $SiO_2$ film on a Si substrate with the thin film thickness being 0.
Figure 9:
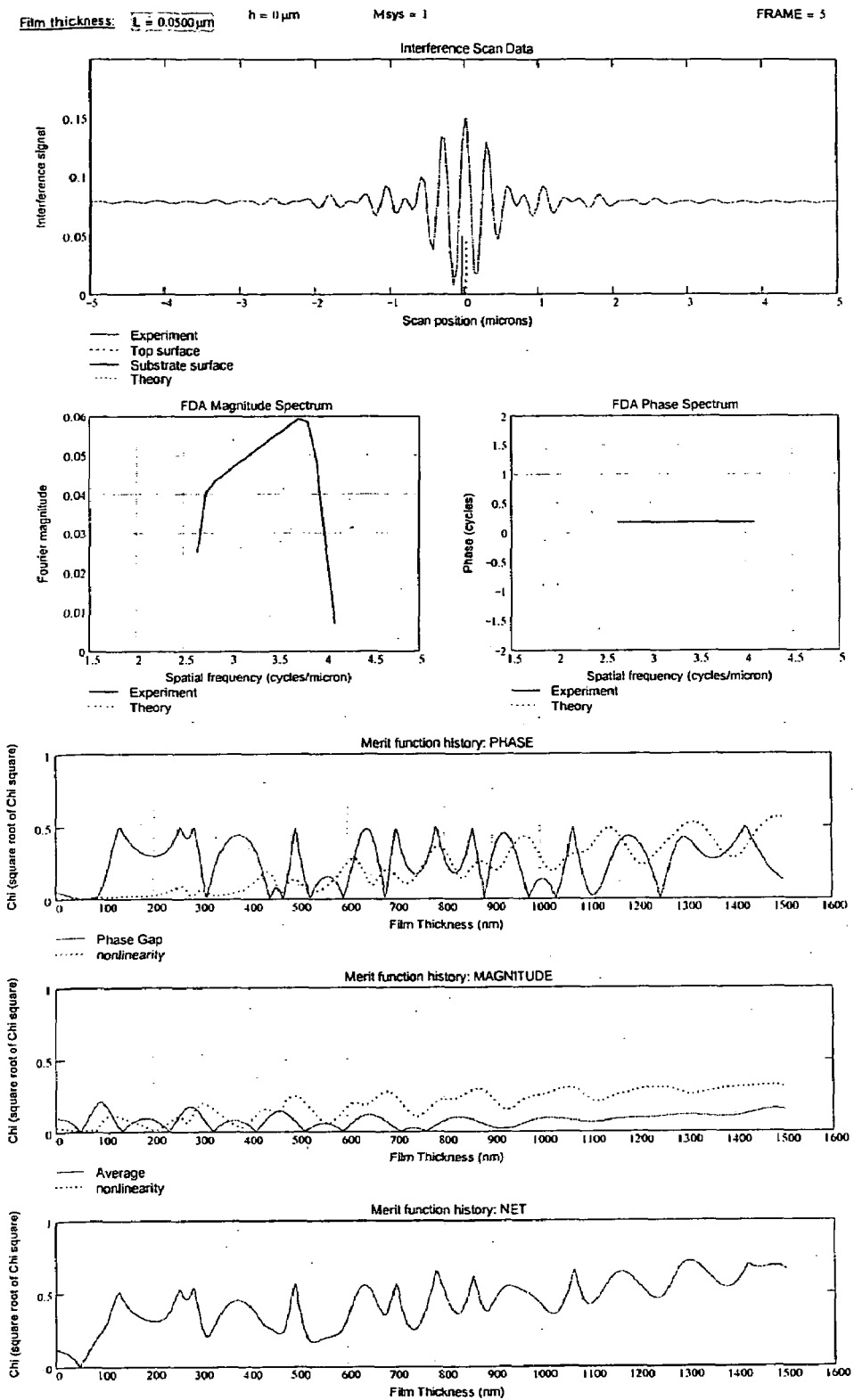
FIG. 9 shows the merit function search procedure for simulation of a $SiO_2$ film on a Si substrate with the thin film thickness being 50 nm.
Figure 10:
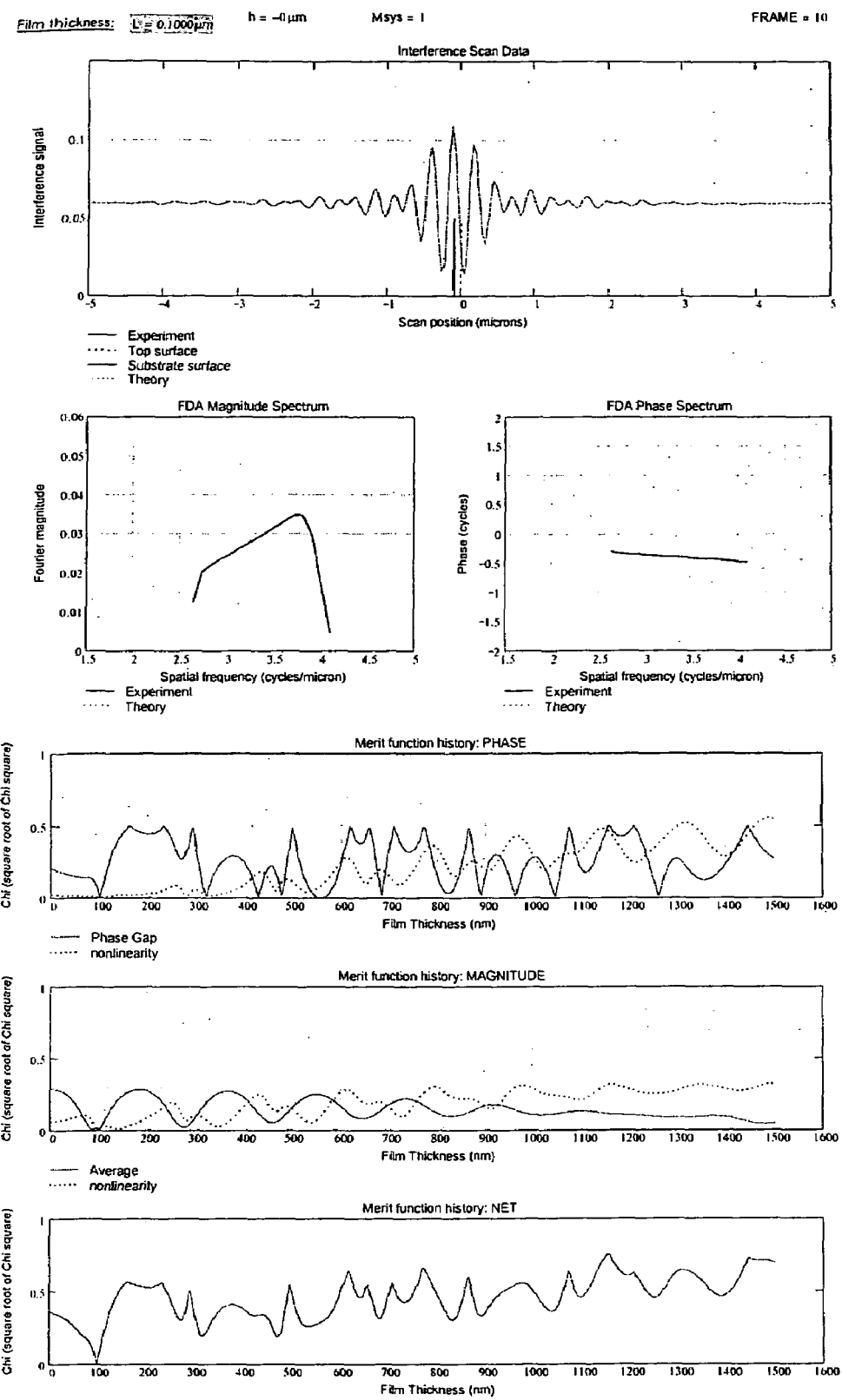
FIG. 10 shows the merit function search procedure for simulation of a $SiO_2$ film on a Si substrate with the thin film thickness being 100 nm.
Figure 11:
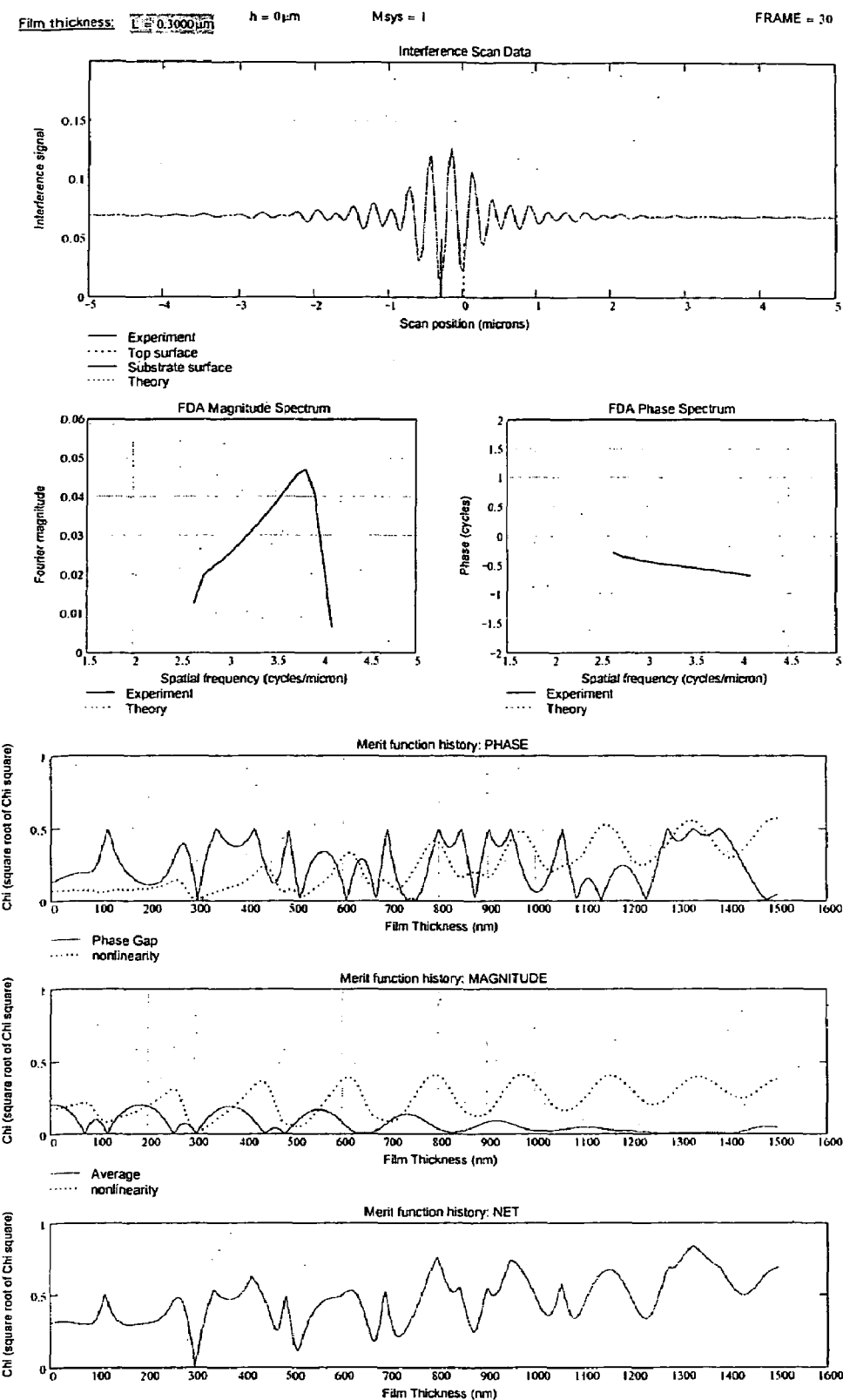
FIG. 11 shows the merit function search procedure for simulation of a $SiO_2$ film on a Si substrate with the thin film thickness being 300 nm.
Figure 12:
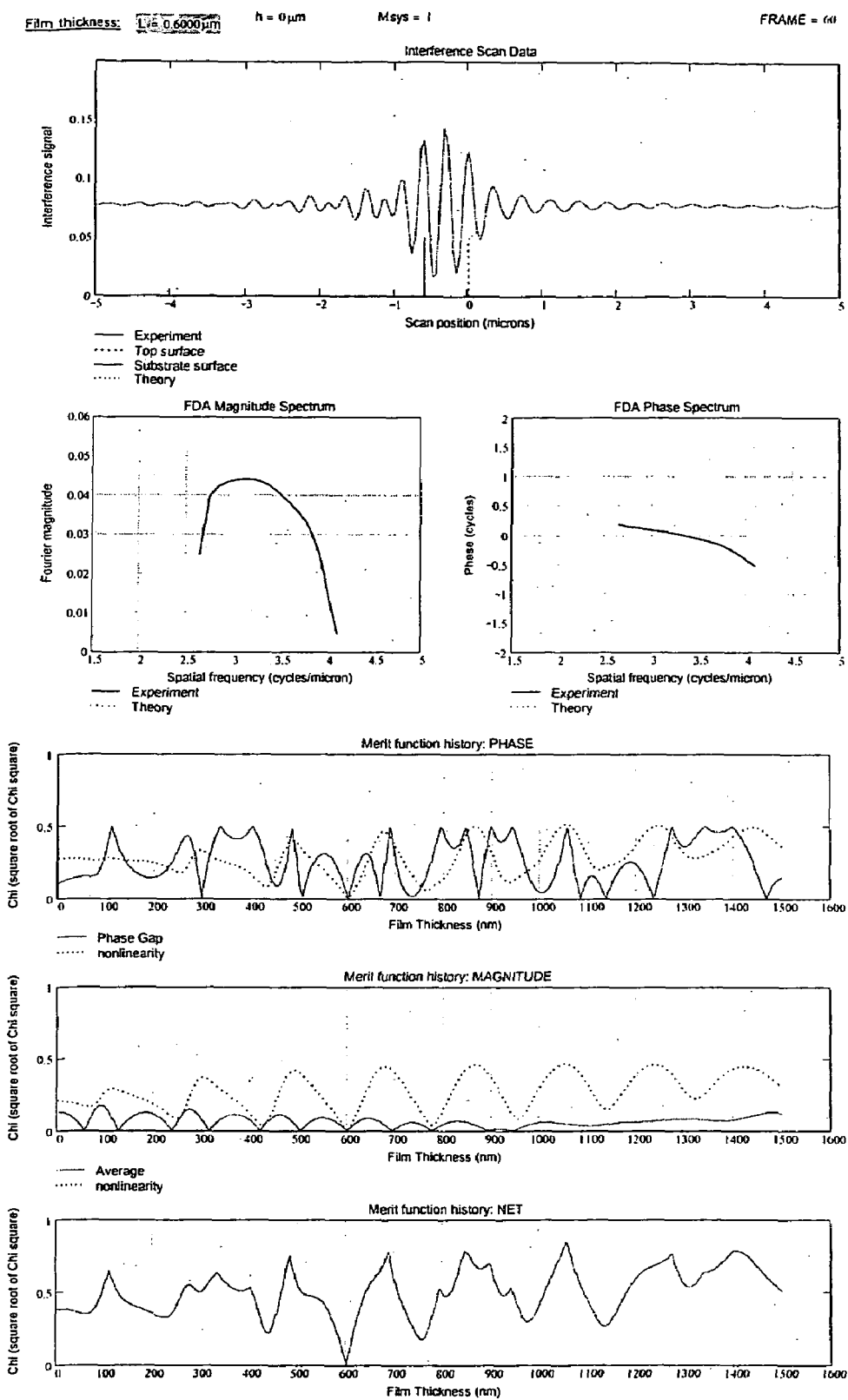
FIG. 12 shows the merit function search procedure for simulation of a $SiO_2$ film on a Si substrate with the thin film thickness being 600 nm.
Figure 13:
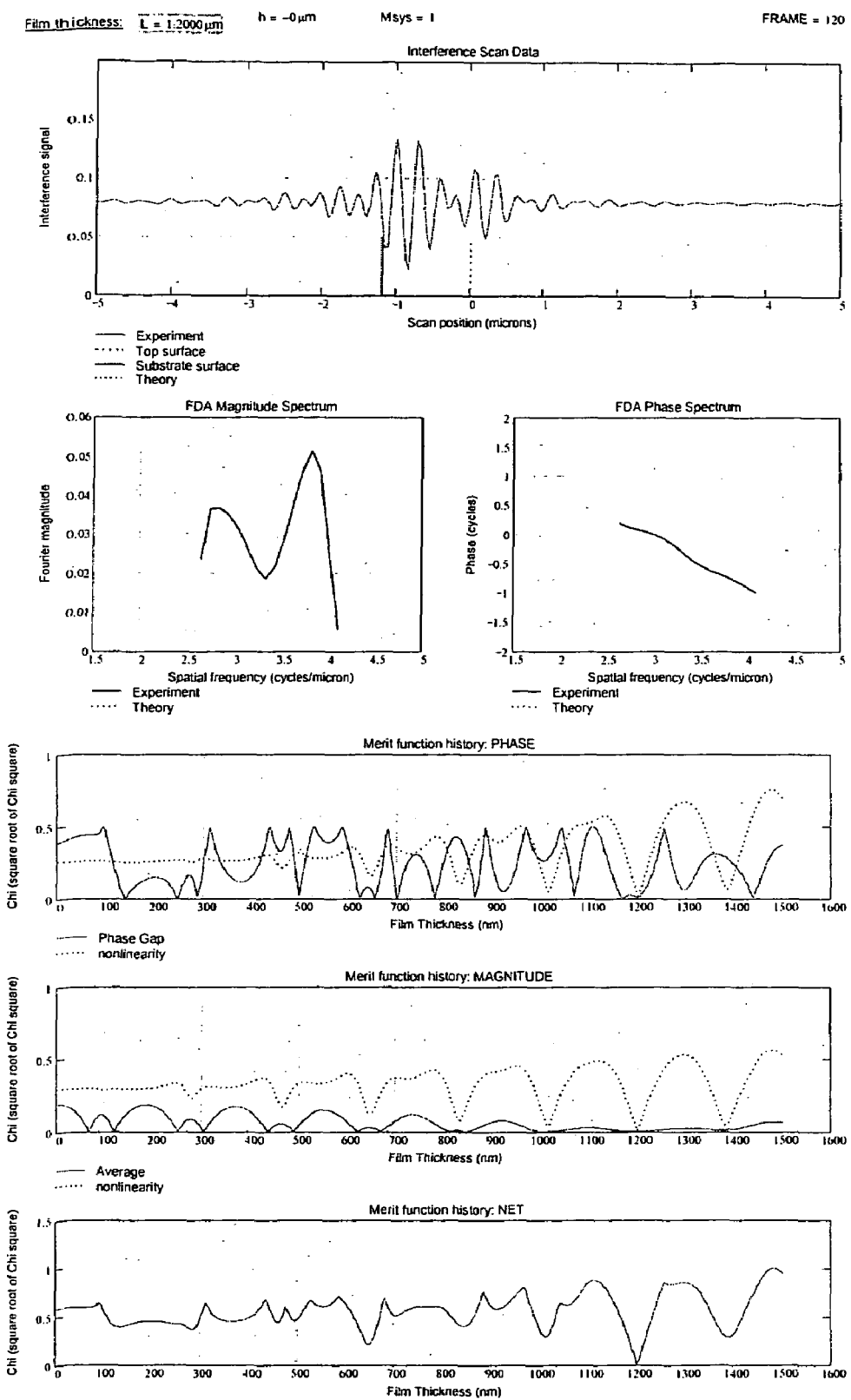
FIG. 13 shows the merit function search procedure for simulation of a $SiO_2$ film on a Si substrate with the thin film thickness being 1200 nm.

FIG. 7 shows two surface types, with and without a thin film. For both cases, we define an effective amplitude reflectivity $z_{\beta,k}$ according to $$z_{\beta,k} = \sqrt{Z_{\beta,k}} \exp(i\omega_{\beta,k}) \tag{66}$$

where $Z_{\beta,k}$ is the intensity reflectivity and $\omega_{\beta,k}$ is the phase change on reflection. The subscripts β,k emphasize a dependency on the directional cosine of the illumination $$\beta_0 = \cos(\psi_0), \tag{67}$$

where $\psi_0$ is the incident angle, and on the wavenumber $$k = (2\pi/\lambda) \tag{68}$$

where λ is the wavelength of the light source. The subscript β will be understood to refer to the first incident directional cosine $\beta_0$.

The surfaces are characterized in part by their index of refraction. The index of the surrounding medium, usually air, is $n_0$. For the simple surface FIG. 7(a) there is only one index $n_1$. For the thin film in FIG. 7(b), there are two surface indices, $n_1$ for the transparent or partially transparent film and $n_2$ for the substrate. Most generally, these refractive indices are complex numbers characterized by a real part and an imaginary part. For example, a typical index, e.g. for chrome at λ=550 nm, is $n_1$=3.18+4.41i, where we are adopting the convention where the imaginary part is defined as positive.

The index of refraction of a material depends on the wavelength. The dispersion in refractive index $n_0$ for the air is not very significant, but is important for many sample surfaces, especially metals. Over small wavelength changes near a nominal k0, most materials have a nearly linear dependence on wavenumber, so that we can write $$n_{1,k} = v_1^{(0)} + k v_1^{(1)} \tag{69}$$

where $v_1^{(0)}$, $v_1^{(1)}$ are the intercept and slope, respectively, for the index of refraction $n_1$ at the nominal wavenumber k0.

The most common use of the refractive index is Snell's law. Referring to FIG. 7(b), the refracted beam angle internal to the film is $$\psi_{1,\beta,k} = \arcsin\left[\frac{n_0}{n_{1,\beta,k}}\sin(\psi_0)\right], \tag{70}$$

where $\psi_0$ is the angle within the medium of index $n_0$ incident on the top surface of the medium of index $n_1$, and $\psi_{1,\beta,k}$ is the angle of refraction. It is possible for these angles to take on complex values if the indices are complex, indicating partially evanescent propagation.

The complex amplitude reflectivity of a boundary between two media depends on the polarization, the wavelength, the angle of incidence and the index of refraction. The s- and p-polarization reflectivities of the top surface of the film in FIG. 7(b) are given by the Fresnel formulae $$\partial_{1,\beta,k}^{s} = \frac{\tan(\psi_0 - \psi_{1,\beta,k})}{\tan(\psi_0 + \psi_{1,\beta,k})} \tag{71}$$

$$\partial_{1,\beta,k}^{p} = \frac{\tan(\psi_0 - \psi_{1,\beta,k})}{\tan(\psi_0 + \psi_{1,\beta,k})} \tag{72}$$

The dependence on β,k results from the angles $\psi_0$, $\psi_{1,\beta,k}$, the exit angle $\psi_{1,\beta,k}$ introducing a k dependency via the refractive index $n_{1,k}$. Similarly, the substrate-film interface reflectivities are $$\partial_{2,\beta,k}^{p} = \frac{\tan(\psi_{1,\beta,k} - \psi_{2,\beta,k})}{\tan(\psi_{1,\beta,k} + \psi_{2,\beta,k})} \tag{73}$$

$$\partial_{2,\beta,k}^{s} = -\frac{\tan(\psi_{1,\beta,k} - \psi_{2,\beta,k})}{\tan(\psi_{1,\beta,k} + \psi_{2,\beta,k})} \tag{74}$$

Note that in the Fresnel equations, if the angle of incidence and refraction are the same, the reflectivity for both polarizations goes to zero.

For a simple surface (no thin film), the sample surface reflectivity is identical to the top-surface reflectivity $$z_{\beta,k} = \theta_{1,\beta,k} \text{ (simple surface, no thin film)} \tag{75}$$

Consequently, the phase change on reflection (PCOR) caused by the surface reflection is $$\omega_{\beta,k} = arg(\theta_{1,\beta,k}). \tag{76}$$

Note that to satisfy the boundary conditions, the s-polarization "flips" upon reflection (=π phase shift for a dielectric), whereas the p-polarization does not. The distinction between polarization states becomes meaningless exactly at normal incidence, which in any case results in a division by zero in the Fresnel equations and a different formula handles this limit case.

When using the plus sign convention for the complex part of the index of refraction, the greater the absorption (complex part), the greater the PCOR $\omega_{\beta,k}$. In other words, a larger absorption coefficient is equivalent to a decrease in effective surface height. This makes intuitive sense—one imagines absorption as a penetration of the light beam into the material prior to reflection, rather than a clean reflection and transmission right at the boundary. Following our usual convention, for which an increase in surface height corresponds to a positive change in the phase difference between the reference and measurement surfaces, a positive surface PCOR subtracts from the interferometer phase.

A thin film is a special case of a parallel plate reflection. The light passes through the top surface partially reflected (see FIG. 7) and continues to the substrate surface where there is a second reflection with a phase delay with respect to the first. However, this is not the end of the story. The light reflected from the substrate is once again partially reflected when passing back up through the top surface, resulting in an additional reflected beam heading south again to the substrate. This goes on in principle forever, with each additional reflection a little weaker than the last. Assuming that all of these multiple reflections survive to contribute to the final surface reflectivity, the infinite series evaluates to $$z_{\beta,k} = \frac{\vartheta_{1,\beta,k} + \vartheta_{2,\beta,k} \exp(2ikL\beta_{1,\beta,k}n_{1,k})}{1 + \vartheta_{1,\beta,k}\vartheta_{2,\beta,k} \exp(2ikL\beta_{1,\beta,k}n_{1,k})} \quad (77)$$

$$\beta_{1,\beta,k} = \cos(\psi_{1,\beta,k}). \quad (78)$$

As a note of clarification, recall the $\beta$ dependency of $\beta_{1,\beta,k}$ refers to a dependency on the incident directional cosine $\beta_0$ in the ambient medium of index $n_0$. The same Eq. (77) applies to both polarization states, with corresponding single-surface reflectivities.

Inspection of these equations shows why conventional FDA processing breaks down in the presence of thin films. Conventional FDA determines surface height by a linear fit to the Fourier phase spectrum weighted by the Fourier power spectrum, using broadband (white) light to generate the Fourier spatial frequency spread. The idea is that the phase evolution comes from the expected linear phase dependence on surface height. Any other constant offset or linear coefficients (e.g., "dispersion") associated with the surface characteristics are removed by system characterization or by simply ignoring those phase contributions that do not change with field position.

This works perfectly fine for simple surfaces. With unpolarized light, and most likely with the circularly-polarized light, the wavelength dependence of the PCOR is nearly linear with respect to wavenumber and constant for a given material. In the presence of a thin film, however, the conventional analysis breaks down. The phase becomes nonlinear and the phase slope becomes sensitive to film thickness, which may be varying across the field of view. Therefore, the present analysis determines key parameters of the surface structure such as film thickness by comparing experimental data to a theoretical prediction, using our knowledge of how e.g. a thin film modulates the reflectivity of the surface.

We now discuss how comparison of experimental data to a library of theoretical predictions provides surface structure parameters such as film thickness and phase change on reflection (PCOR). In the case of a film of unknown thickness, the library for a single surface type, e.g. $SiO_2$ on Si, would range over many possible film thicknesses. In frequency domain embodiments, the idea is to search this library for a match to those characteristics of the FDA spectra that are independent of surface topography, for example, a distinctive structure to the magnitude spectrum resulting from a thin-film interference effect. The computer then uses the library spectrum to compensate the FDA data, allowing for a more accurate surface topography map.

In one embodiment, the library contains example FDA spectra for surface structures, each spectrum providing a series of complex coefficients $\rho_K$ representing Fourier coefficients as a function of spatial frequency K. These spectra are the Fourier transforms of intensity data $I_{\zeta,h}$ acquired during a scan $\zeta$ of the optical path length of an interferometer. The spatial frequency K is proportional to the angular wavenumber $k=2\pi/\lambda$ for a segment of the source light spectrum, the index of refraction $n_0$ of the ambient medium, and the directional cosine $\beta=\cos(\psi)$, where $\psi$ is the angle of incidence for a ray bundle directed to the object surface:

$$K=2\beta k n_0. \quad (79)$$

The $\rho_K$ coefficients for the prediction library include the optical properties of the surface that can influence the appearance of the FDA spectra, with the exception of surface height.

Predicting the FDA spectra involves an integral representing the incoherent sum of ray bundles over a range of incident angles $\psi$ and angular wavenumbers k for the source light. As described above, the numerical integration can reduce to a computationally-efficient single sum over N angular wavenumbers k, weighted by a factor $\Gamma_{K,k}$:

$$\rho_{K>0} = \frac{\sqrt{N}}{\Upsilon} \sum_k H_{k-K/2n_0} \sqrt{R_{K,k}Z_{K,k}} \exp[i(\upsilon_{K,k} - \omega_{K,k})]\Gamma_{K,k} \quad (80)$$

$$\rho_0 = \frac{\sqrt{N}}{\Upsilon} \sum_{K \geq 0} \sum_k H_{k-K/2n_0}(R_{K,k} + Z_{K,k})\Gamma_{K,k} \quad (81)$$

The weighting factor is $$\Gamma_{K,k} = \frac{KU_{K,k}V_k}{4k^2 n_0^2}, \quad (82)$$

where $V_k$ is the source spectrum and $U_{K,k}$ is the pupil-plane light distribution. The corresponding normalization $\Upsilon$ is the sum over all spatial frequencies of the weighting factor $$\Upsilon = \sum_{K \geq 0} \sum_k H_{k-K/2n_0} \Gamma_{K,k} \quad (83)$$

where $\Upsilon$ is a normalization to be defined shortly and H is the Heaviside step function.

The distinctive characteristics of an object surface structure, particularly of a thin film, enter into the spectrum $\rho_K$ through the object-path phase $\omega_{K,k}$ and reflectivity $Z_{K,k}$, as detailed above. Equally important are the reference-path phase $\upsilon_{K,k}$ and reflectivity $R_{K,k}$, which depend on the scanning interferometer itself. Such factors can be determined by theoretically modeling the scanning interferometer or by calibrating it with a test sample having known properties, as described further below.

The typical prediction library for a thin film is a series of spectra $\rho_K$ indexed by film thickness L. The stored spectra cover only a narrow spatial frequency region of interest (ROI), usually 15 or 16 values for a 256-frame intensity data acquisition, the remainder of the values outside this ROI being zero. The limits of the ROI follow from the definition of the spatial frequency:

$$K^{min} = 2\beta^{min} k^{min} n_0 \quad (84)$$

$$K^{max} = 2\beta^{max} k^{max} n_0 \quad (85)$$

A typical range of spatial frequencies for a scanning interferometer based on a 100xMirau objective and a narrow bandwidth, 500-nm light source is 2.7 µm$^{-1}$ to 4.0 µm$^{-1}$. For computational efficient, a dense look up table, indexed by 0.5 to 5 nm between sample spectra, can be used rather than an analytical search routine that involves recalculation using Eqs. (80)–(83) several times for each pixel.

The library search involves the following steps: (1) Select a predicted FDA spectrum from the library corresponding to a specific surface type, (2) calculate how closely this spectrum matches the experimental data using a merit function, then (3) repeat through several or all of the library data sets to determine which theoretical spectrum provides the best match. What we are looking for is a "signature" in the frequency domain that relates uniquely to surface characteristics such as thin films, dissimilar materials, step structures, roughness, and their interaction with the optical system of the interferometer. This comparison therefore explicitly filters away the linear rate of change of phase with spatial frequency, which is the one characteristic of the FDA spectrum that varies directly with surface topography and is therefore irrelevant to the library search.

In comparing spectra, there is a benefit to separating the phase and magnitude contributions to the merit calculation. Thus for the theory, we have $$P_K = |\rho_K| \quad (86)$$

$$\phi_K = \text{connect}_K[\arg(\rho_K)], \quad (87)$$

where connect$_K$ is a function that removes 2-$\pi$ steps in the spatial frequency dependence of $\phi_{K,h}$. For the experimental data we have $$P_K^{ex} = |q_{K,h}^{ex}| \quad (88)$$

$$\phi_{K,h}^{nex} = \text{connect}_K[\arg(q_{K,h}^{ex})], \quad (89)$$

The double prime for $\phi_K^{"ex}$ indicates an uncertainty in the fringe order from both pixel to pixel and overall with respect to the starting point in the scan. The experimental data necessarily include a slope term related to the local surface height; this is the reason for the use of the q symbol instead of the $\rho$ symbol.

For a specific set of trial surface parameters, we can calculate a phase difference $$\varsigma_{K,h}^n = \phi_{K,h}^{nex} - \phi_K \quad (90)$$

The phase difference $\varsigma"_{K,h}$ is the compensated FDA phase, assuming that the trial parameters are correct. A good match of theory to experiment yields a phase $\varsigma"_{K,h}$ that in principle is a simple linear function of spatial frequency K with an intercept of zero (i.e., zero phase gap). Thus, looking ahead, the successfully compensated phase $\varsigma"_{K,h}$ is what we shall eventually feed downstream to a conventional FDA analysis, which assumes that the slope of the phase in frequency space is directly proportional to surface height.

Based on the observations of the previous paragraph, there are two features of interest in the compensated phase $\varsigma"_{K,h}$ that allow us to evaluate the match of theory to experiment independent of surface height. The first is the phase gap A" or K=0 intercept value $\varsigma"_{K=0,h}$ obtained by a linear fit, and the second is the residual nonlinearity with respect to wavenumber after a linear fit. Corresponding merit functions are, for example, $$\chi_\phi = \left[\frac{A"}{2\pi} - \text{round}\left(\frac{A"}{2\pi}\right)\right]^2 \quad (91)$$

$$\chi_{\phi non} = \frac{\sum\limits_{k>0}(\varsigma"_{K,h} - \sigma_h K - A")^2 P_{K,h}^{ex}}{\sum\limits_{K>0} P_{K,h}^{ex}} \quad (92)$$

where $\sigma_h$ is the slope of the (magnitude weighted) linear fit to the compensated phase $\varsigma"_{K,h}$. The round( ) function in Eq. (91) limits the phase gap A" to the range $\pm\pi$.

Although a library search can proceed using phase information alone, i.e. by minimizing one or both of the merit function values $\chi_\phi$ and/or $\chi_{\phi non}$, we also have important and useful signatures in the Fourier magnitude. The magnitude is particularly interesting in that it is inherently independent of surface height. Thus for example, we can define in approximate analogy with the phase merits the following magnitude merit functions:

$$\chi_P = \left[\frac{\sum\limits_{K>0}(P_{K,h}^{ex} - P_{K,h})}{\sum\limits_{K>0}(P_{K,h}^{ex} + P_{K,h})}\right]^2 \quad (93)$$

$$\chi_{Pnon} = \frac{\sum\limits_{K>0}(\Omega^{-1} P_{K,h}^{ex} - P_{K,h})^2}{\sum\limits_{K>0}(\Omega^{-1} P_{K,h}^{ex} + P_{K,h})^2} \quad (94)$$

where $\Omega$ is the empirical scaling factor $$\Omega = \sum_{K>0} P_{K,h}^{ex} \bigg/ \sum_{K>0} P_{K,h}. \quad (95)$$

The merit $\chi_P$ is most closely related to the overall reflectivity of the object surface, independent of spatial-frequency dependence, whereas $\chi_{Pnon}$ expresses how well the theoretical and experimental magnitude plots match in shape.

The magnitude merit functions $\chi_P$ and/or $\chi_{Pnon}$ are in addition to or even in place of the phase merits $\chi_\phi$ and/or $\chi_{\phi non}$. A general library search merit function is therefore $$\chi = w_\phi \chi_\phi + w_{\phi non} \chi_{\phi non} + w_P \chi_P + w_{Pnon} \chi_{Pnon} \quad (96)$$

where the w are weighting factors. In principle, one can determine the weights in Eq. (96) knowing the standard deviation for the various parameters. A more empirical approach is to try out various weights on real and simulated data and see how well they work. For the examples that follow, we select equal weights $w_\phi=w_{\phi non}=w_P=w_{Pnon}=1$ for all merit contributions.

The examples in FIGS. 8–13 illustrate the merit-function search procedure for six SiO$_2$ on Si film thicknesses: 0, 50, 100, 300, 600, and 1200 nm, respectively. A single library for all examples encompasses the range from 0 to 1500 nm in 2-nm intervals. The data are simulations, free of noise. As in all the examples described herein, the scan step is 40 mm, the source wavelength is 498 mm, and the source gaussian FWHM is 30 nm (quasi-monochromatic).

The most interesting aspect of these simulated searches is the behavior of the four merit functions. Generally, we observe that inclusion of these four functions helps to reduce the ambiguity in the final merit values, there being a strong periodicity for individual merit values as a function of film thickness. Another general observation is that the merits based on nonlinearity, both in phase and magnitude, are most effective at 300 nm and above, whereas the phase gap and average magnitude are dominant below 300 run film thickness. This shows that the $\chi_\phi, \chi_P$ merit functions are especially useful to the really thin films, which places importance on system characterization, which couples directly into the phase gap and magnitude results.

Once we determine the thin film thickness (or identify the material or other uses for the algorithm), FDA processing proceeds in the usual way, using however the corrected FDA phase $\zeta''_{K,h}$ instead of the original experimental phase data. In principle, if the modeling has been successful, $\zeta''_{K,h}$ should be free of nonlinearities and the phase gap should be zero. The next step therefore is a linear fit to the phase spectrum $\zeta''_{K,h}$. It appears more effective for high-NA FDA to use the magnitude spectrum $P_K$ in place of magnitude squared. The fit provides for each pixel a slope $$\sigma_h \approx d\zeta''_{K,h}/dK \quad (97)$$

and an intercept (phase gap)

$$A'' \approx \zeta''_{K=0,h}. \quad (98)$$

Note that the phase gap A" carries the double prime inherited from the fringe order uncertainty in the phase data. The slope $\sigma_h$ is free of this uncertainty. From the intercept A" and the slope $\sigma_h$, we define for a specific mean or nominal spatial frequency K0 a "coherence profile"

$$\Theta_h = \sigma_h K0 \quad (99)$$

and a "phase profile"

$$\theta''_h = \Theta_h + A''. \quad (100)$$

We then removes the pixel-to-pixel fringe order uncertainty in the phase $\theta''_h$:

$$\theta' = \theta'' - 2\pi \, \text{round}\left[\frac{A'' - \alpha'}{2\pi}\right] \quad (101)$$

where $\alpha'$ is an approximation to the original phase gap A" that is free of pixel-to-pixel $2\pi$ steps.

Finally, the height profile follows from $$h' = \theta'/K0. \quad (102)$$

Note that it is not necessary to subtract the phase offset $\gamma$, because it has already been done in generating the compensated phases $\zeta_{K,h}$.

Figure 14:
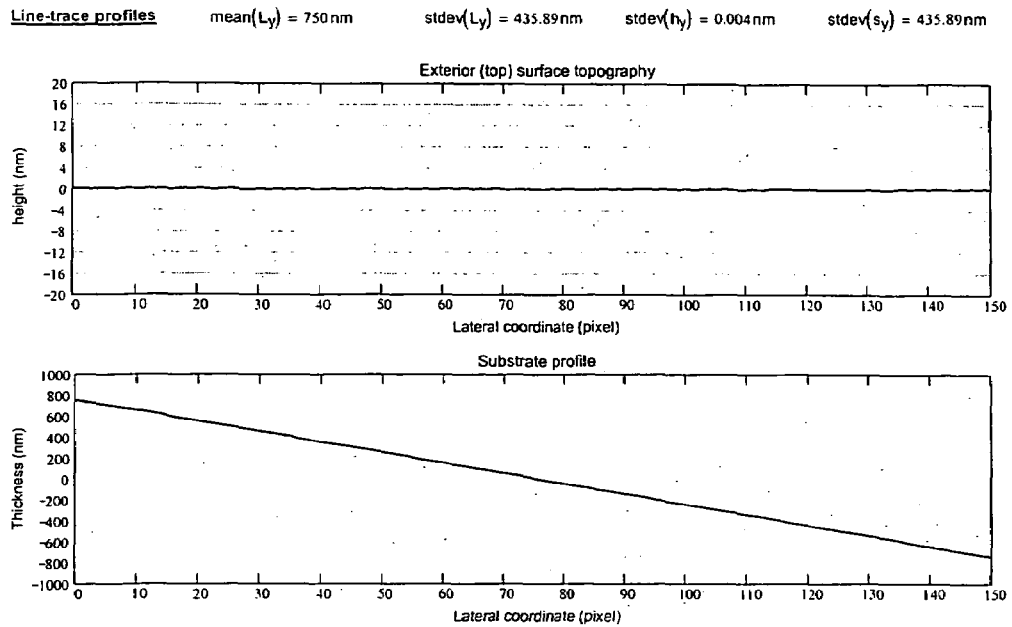
FIG. 14 shows the surface and substrate profiles determined for a simulation of a $SiO_2$ on Si thin film in which the film thickness varies uniformly from 0 to 1500 nm in 10-nm increments per pixel, with the top surface always at zero.

The first example of a surface topography measurement (FIG. 14) is a pure simulation. The surface topography is everywhere zero, but there is an underlying film layer that progresses from 0 to 1500 nm in 10 nm increments. Using the same prediction library as in FIGS. 8–13, this test demonstrates unambiguous determination of film thickness throughout the range of the prediction library, albeit for perfect, noise-free data.

Figure 15:
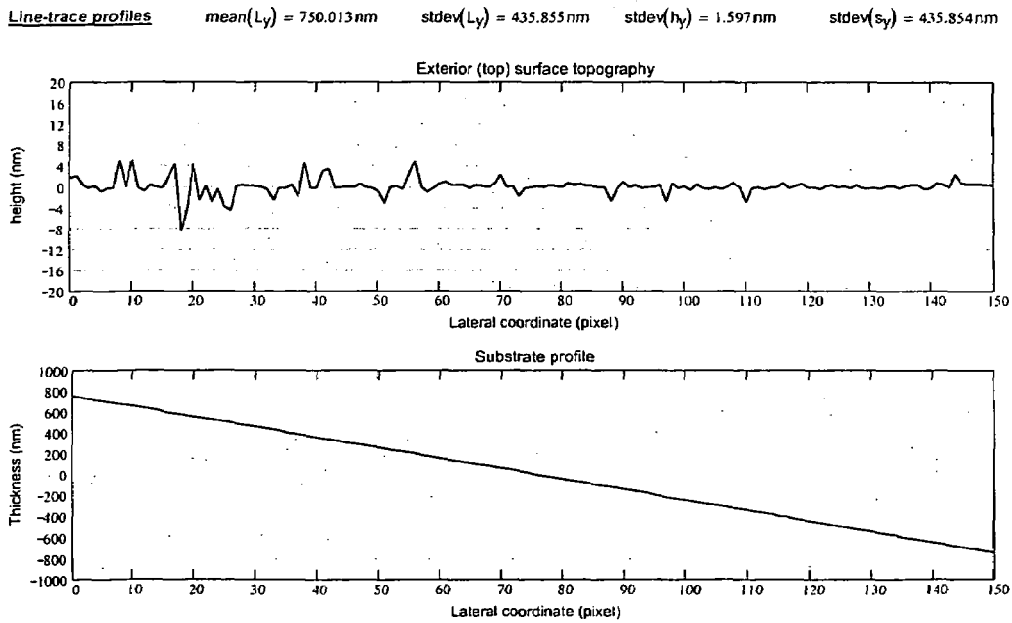
FIG. 15 shows the surface and substrate profiles determined for a simulation identical to that in FIG. 14 except that random noise has been added (2-bits rms out of an average 128 intensity bits).

The next example (FIG. 15) is also a simulation, but with additive noise. The random additive noise is gaussian, with a standard deviation of 2 bits out of an average 128 intensity bits, which looks to be typical of real data. The results are clearly satisfactory despite the significant difference in reflectivity between SiO$_2$ and Si (4% to 45%).

We now address system characterization.

We define a phase offset $\gamma_{sys}$ and a linear dispersion $\tau_{sys}$ using data collected during a system characterization procedure. To include system characterization data, we correct the Fourier-transformed experimental data $q_K^{ex}$ prior to the library search and prior to any other FDA processing on a pixel-by-pixel basis using $$q_{K>0}^{ex} = M^{-1} \exp[-i\gamma_{sys} - i(K-K0)\tau_{sys}] q_{K>0}^{ex}. \quad (103)$$

where K0 is the nominal spatial frequency, which represents the nominal spectral frequency for the FDA data set, as identified e.g. by locating the midpoint of the ROI. Note that the theoretical library remains unchanged. The scaling coefficient M (greek capital "M") is a new system characterization that makes it possible to use object surface reflectivity as a parameter in the library search.

The phase offset $\gamma_{sys}$ and the system phase gap $A_{sys}$ as a functions of field position can be stored as a function of field position, and calculate the true system dispersion according to $$\tau_{sys} = (\gamma_{sys} - A_{sys})/K0. \quad (104)$$

The magnitude coefficient M is also field dependent.

The creation of system characterization data proceeds in a manner similar to that described above for the object sample. We move to an artifact having known characteristics, measure it, and determine the system characterization by looking at how the results differ from what we would expect for a perfect system. Specifically, using a known sample for which the correct library entry is predetermined, we generate the phase gap A" as in Eq. (98) and a final height h' as in Eq. (102). Then, assuming a perfectly flat artifact, we calculate the system phase offset $$\Gamma_{sys} = K0h' \quad (105)$$

and the system phase gap $$A_{sys} = \text{connect}_{xy}(A'') \quad (106)$$

where connect$_{xy}$( ) is pixel-to-pixel phase unwrapping. The magnitude map is $$M_{sys} = \sum_{K>0} P_{K,h}^{ex} \Big/ \sum_{K>0} P_{K,h}. \quad (107)$$

In some embodiments, several system characterizations can be averaged, perhaps using artifacts having similar surface structure to the final application (e.g. SiO2 on Si) over a range of sample types.

In much of the description and simulations above we have focused on thin film surface structures, however, the analysis is also applicable to other types of complex surface structures. In what follows we show how the scanning interferometry data can be analyzed to account for surface structures that are smaller than the optical resolution of the scanning interferometer microscope. The optical resolution is ultimately limited by the wavelength of the light source and the NA of the light collection optics.

Figure 16:
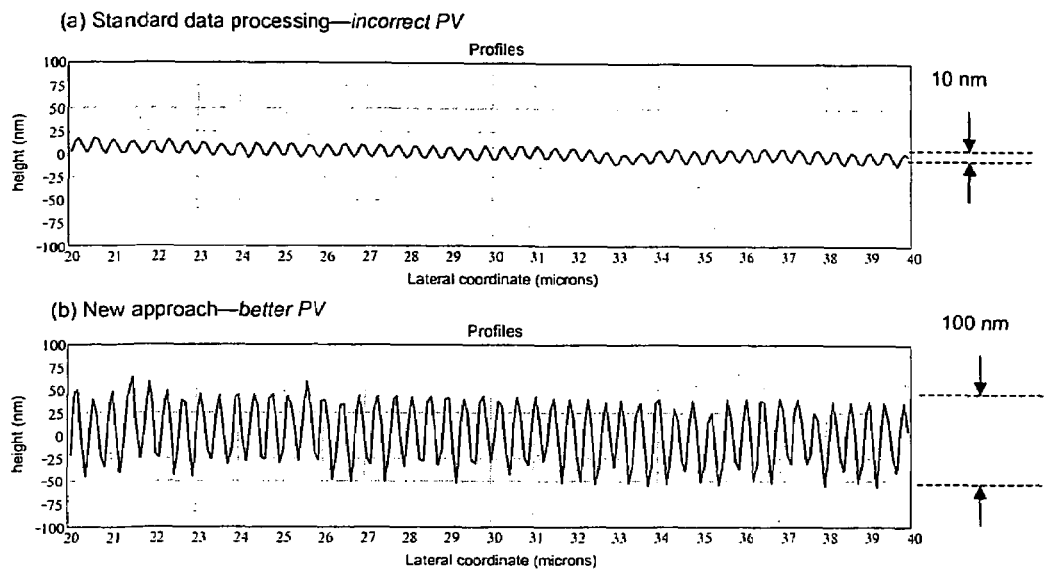
FIG. 16 shows surface height profiles determined using conventional FDA analysis (FIG. 16a) and a library search method described herein (FIG. 16b) for a 2400 line per mm grating having an actual peak-to-valley modulation depth of 120 nm.

FIG. 16a shows height profiles determined from actual scanning interferometry data of a 2400 lines per mm (lpmm) grating having a peak-to-valley (PV) modulation depth of 120 nm using a light source at a 500-nm nominal wavelength. The top profile in FIG. 16a shows the height profile determined using a conventional FDA analysis. The conventional analysis indicates a PV modulation depth of only about 10 nm, greatly underestimating the actual modulation depth. This inaccuracy occurs because the grating has features at the limit of the optical resolution of the 500-nm instrument. This is so even though the pixel resolution of the camera in the instrument is more than sufficient to accurately resolve the grating.

One way of thinking about this effect is that the scanning interferometry signal for a first camera pixel generally corresponding to a first surface location also includes contributions from adjacent surface locations when those additional surface locations have surface features sufficiently sharp relative to the light wavelength to diffract light to the first pixel. The surface height features from those adjacent surface locations corrupt conventional analysis of the scanning interferometry signal corresponding to the first surface location.

Figure 17:
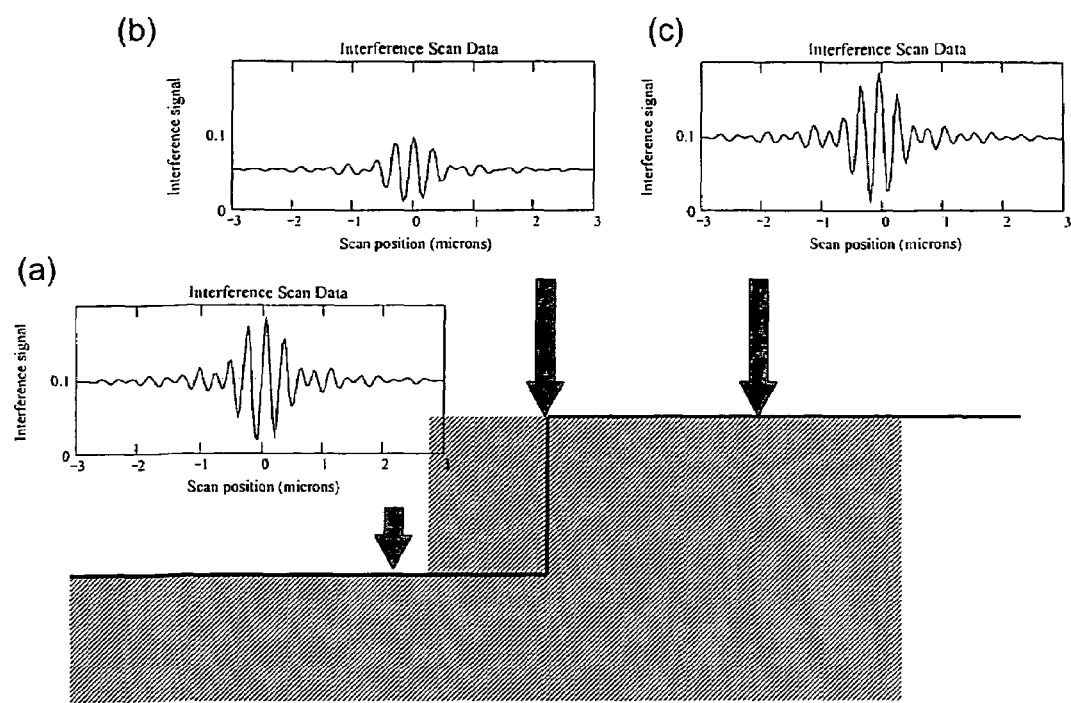
FIG. 17 shows distortions caused by an under-resolved step height in a scanning interference signals for pixels corresponding to various surface locations near the step height.
Figure 18:
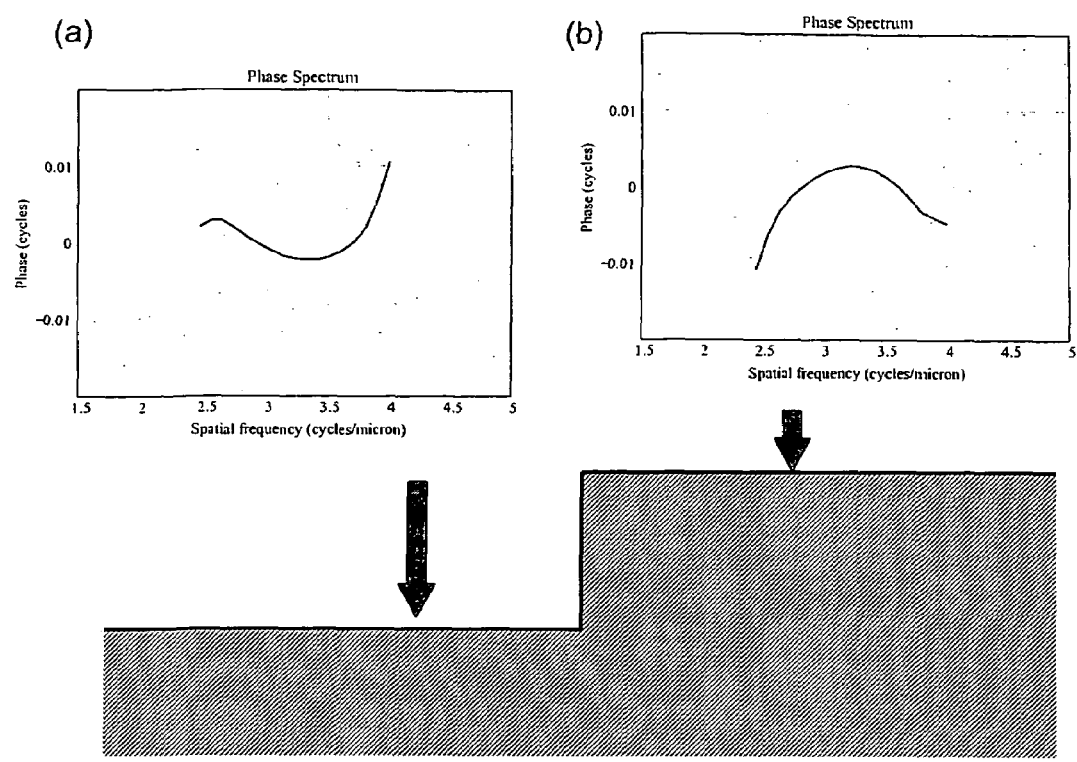
FIG. 18 shows nonlinear distortions in the frequency domain phase spectra for pixels corresponding to surface locations to the left (FIG. 18a) and the right (FIG. 18b) of the under-resolved step height in FIG. 17.

At the same time, however, this means that the scanning interferometry signal corresponding to the first surface location includes information about the complex surface features nearby. FIG. 17 illustrates this by showing the scanning interferometry signal from pixels corresponding to various locations about a step height feature. For the signal in (a) the step height is to the right of the pixel and higher, for the signal in (b) the step passes directly through the pixel, and for the signal in (c) the step is to the left of the pixel and is lower. One signature that is immediately apparent in the signals is the reduction in fringe contrast in (b) relative to (a) and (c). For example, if the step height was equal to one-quarter of the wavelength and the pixel location corresponded exactly to the position of the step height, the fringe contrast in (b) should disappear entirely because interference from the two sides of the step would exactly cancel one another. There is also much information in the signals in shown in (a) and (c). For example, FIG. 18 shows the nonlinear distortions in the frequency domain phase spectra for the signals (a) and (c) of FIG. 17, respectively, resulting from the nearby step height. These spectra are indicated as (a) and (b), respectively, in FIG. 18. In the absence of the step height, the frequency domain phase spectra would be linear. Thus, the nonlinear features in the frequency domain phase spectrum for pixels corresponding to surface locations adjacent to the step height nonetheless include information about the step height.

To more accurately measure the surface profile of a test surface in the presence of such under-resolved surface features, we can use the library searching technique described above for thin films. For example, for the case of a test surface with an under-resolved grating, a series of model FDA spectra are generated for different values of the PV modulation depth and offset position. As in the thin film examples, the surface height for the model spectra remains fixed. The analysis then continues as in the thin film examples above, except that rather than the model spectra being parameterized by thin film thickness, they are parameterized by modulation depth and offset position. Comparison between signatures of the FDA spectra for the actual test surface and the different model spectra can then be used to determine a match. Based on the match, distortions in the actual FDA spectrum for each pixel caused by the presence of the grating are removed so that the surface height for each pixel can be determined using conventional processing. The results of such an analysis using the same merit functions as described above for the thin films are shown in FIGS. 16b and 19b.

Figure 19:
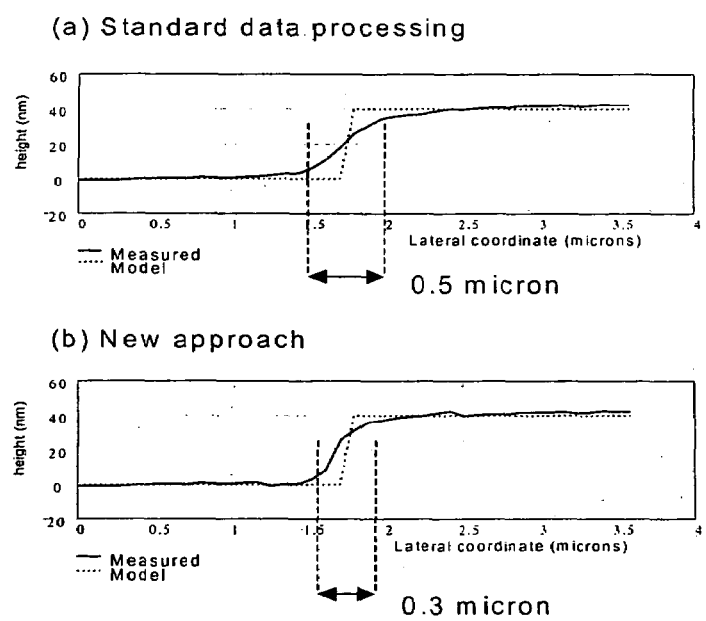
FIG. 19 shows surface height profiles determined using conventional FDA analysis (FIG. 19a) and a library search method described herein (FIG. 1b) for an under-resolved step height.

FIG. 16b shows the height profile determined using the library search analysis for 2400 lines per mm grating described above with reference to FIG. 16a. The same data was used in the FIGS. 16a and 16b, however, the library search analysis determined the PV modulation depth for the grating to be 100 nm, much closer to the actual 120-nm modulation depth than the 10-nm result determined by conventional FDA processing in FIG. 16a. FIGS. 19a and 19b show a similar analysis for a simulation with a discrete step height and assuming a nominal 500-nm light source. FIG. 19a shows the height profile determined using conventional FDA processing (solid line) compared to the actual height profile for the simulation (dotted line). FIG. 19b shows the height profile determined using the library search method (solid line) compared to the actual height profile for the simulation (dotted line). The parameters for the model spectra in the library search were location and step height magnitude. As illustrated, the library search analysis improves lateral resolution from about 0.5 microns to about 0.3 microns.

In the detailed analyses described above the comparison between information in the actual data and information corresponding to the different models has occurred in the frequency domain. In other embodiments, the comparison can be made in the scan coordinate domain. For example, while changes in the absolute position of the fringe contrast envelope is generally indicative of changes in surface height at a first surface location corresponding to the signal in question, the shape of the signal (independent of its absolute position) contains information of complex surface structure, such as underlying layers at the first surface location and/or surface structure at adjacent locations.

One simple case is to consider to the magnitude of the fringe contrast envelope itself. For example, when a thin film thickness is very small relative to the range of wavelengths produced by the light source, the interference effects produced by the thin film become wavelength independent, in which case thin film thickness directly modulates the magnitude of the fringe contrast envelope. So, in general, the fringe contrast magnitude can be compared to that for models corresponding to different thin film thicknesses to a identify a match for a particular thin film thickness (taking into account systematic contributions from the interferometer itself).

Another simple case is to look at the relative spacings of the zero crossings of the fringes under the fringe contrast envelope. For a simple surface structure illuminated with a a symmetric frequency distribution, the relative spacings between the different zero crossings should be nominally the same. Variations in the relative spacings are therefore indicative of complex surface structure (when taking into account systematic contributions from the interferometer itself) and can compared to models for different complex surface structures to identify a match to a particular surface structure.

Another case is to perform a correlation between the scan-domain signal and the scan-domain signals corresponding to different models of the test surface. A match generally corresponds to the correlation that has the highest peak value, which indicate the model whose scan-domain signal has a shape most similar to the shape of the actual signal. Note that such analysis is generally independent of surface height because a difference between the surface height of the actual sample and that of each model only shifts the location of peak in the correlation function, but does not effect, in general, the peak value itself. On the other hand, once the correct model is identified, the location of the peak in the correlation function of the correct model yields the surface height for the test sample, without the need for further analysis (such as conventional FDA).

Like the analysis in the spatial frequency domain, an analysis in the scan-coordinate domain can be used for many different types of complex surfaces, including not only thin films, but also other complex surface structures such as under-resolved surface height features as described above.

We now describe in detail a scan-coordinate library search analysis the involves a correlation between the signal for the test sample and corresponding signals for various models of the test sample.

The approach sets aside any assumptions about the interference pattern other than to say that all pixels in a data set corresponding to surface locations with the same complex surface characteristics contain the same basic, localized interference pattern, only shifted in position (and possibly rescaled) for each pixel. It does not matter what the signal actually looks like, whether it is a gaussian envelope or has a linear phase behavior in the frequency domain or whatever. The idea is to generate a sample signal or template that represents this localized interference pattern for different models of complex surface structures for the test object, and then for each pixel, find the model whose localized interference pattern best matches the shape of the actual localized interference pattern, and for that model, find the scan position within the data set that provides the best match between the interference pattern template and the observed signal—which gives the surface height. Several techniques are available for pattern matching. One approach is to mathematically correlate each template with the data. Using a complex (i.e. real plus imaginary) template function for each model, we recover two profiles, one closely associated with the envelope of the signal and the other associated with the phase of the underlying carrier signal.

In one embodiment, for example, the analysis for each pixel would be include: (1) selecting a test template from a library of templates calculated or recorded for a specific value of an adjustable parameter, such as film thickness; (2) finding the local surface height using the selected test template and a correlation technique (an example of which is described below); (3) recording the peak merit function value for the selected test template based on the correlation technique; (4) repeating steps 1–3 for all or a subset of the templates in the library; (5) determining which test template provides the best match (=highest peak merit function value); (6) recording the value for the adjustable parameter for the best-matched template (e.g., thin film thickness); and (7) recalling the height value that provided the peak match position within the data trace.

We now describe a suitable correlation technique based on a complex correlation. For each model of the test surface we generate a template interference pattern $$I_{temp}^j(\zeta) = m_{temp}^j(\zeta)\cos[K_0\zeta + \phi_{temp}^j(\zeta)] \quad (108),$$

where the index j indicates the specific model for the template pattern. The functions $m_{temp}^j(\zeta)$ and $\phi_{temp}^j(\zeta)$ characterize the complex surface structure, but are independent of surface height at the location corresponding to the signal, which is set to zero. In preferred embodiments, the functions $m_{temp}^j(\zeta)$ and $\phi_{temp}^j(\zeta)$ also account for systematic contributions from the interferometer. We then use a complex representation for the template pattern:

$$\tilde{I}_{temp}^j(\zeta) = m_{temp}^j(\zeta)\exp[i(K_0\zeta + \phi_{temp}^j(\zeta))] \quad (109).$$

We further use a window function to select a particular portion of the complex template function:

$$w(\zeta) = \begin{cases} 1 & \text{for } \zeta_{start} \leq \zeta \leq \zeta_{stop} \\ 0 & \text{otherwise} \end{cases} \quad (110)$$

$$\tilde{I}_{pat}^k(\zeta) = w(\zeta)\tilde{I}_{temp}^k(\zeta) \quad (111)$$

For example, an appropriate window might be $$\zeta_{start} = -\frac{\Delta\zeta}{2} \quad (112)$$

$$\zeta_{stop} = +\frac{\Delta\zeta}{2}$$

where the window width $\Delta\zeta$ could be set by hand.

Now that we have an interference pattern template $\tilde{I}_{pat}^j$ we are ready to use it for comparison to an actual data set. In preparation for this, it will be handy to generate a complex signal $\tilde{I}_{ex}$ starting from a real experimental data set $$I_{ex}(\zeta,x) = DC_{ex}(x) + \ldots AC_{ex}(x)m_{ex}[\zeta-h_{ex}(x)]\cos\{-[\zeta - h_{ex}(x)]K_0 + \phi_{ex}[\zeta-h_{ex}(x)]\}. \quad (113)$$

The Fourier transform of this signal is $$q_{ex}(K,x) = FT\{I_{ex}(\zeta,x)\} \quad (114)$$

$$q_{ex}(K,x) = \delta(K)DC_{ex}(x) + \tfrac{1}{2}AC_{ex}(x)[G^*_{ex}(-K-K_0,x) + G_{ex}(K-K_0,x)] \quad (115)$$

where $$G_{ex}(K) = FT\{m_{ex}(\zeta)\exp[i\phi_{ex}(\zeta)]\}\exp[iKh_{ex}(x)]. \quad (116)$$

We then construct a partial spectrum from the positive-frequency portion of the spectrum:

$$\tilde{q}_{ex}(K) = AC_{ex}(x)G_{ex}(K-K_0,x). \quad (117)$$

The inverse transform is then $$\tilde{I}_{ex}(\zeta) = FT^{-1}\{\tilde{q}_{ex}(K)\} \quad (118)$$

$$\tilde{I}_{ex}(\zeta,x) = AC_{ex}(x)m_{ex}[\zeta-h_{ex}(x)]\exp\{-i[\zeta-h_{ex}(x)]K_0 + i\phi_{ex}[\zeta-h_{ex}(x)]\} \quad (119)$$

Here, the real part of this complex function $\tilde{I}_{ex}$ is the original experimental data $I_{ex}$. Further, the phase and envelope are separable by simple operations, e.g. we can access the product of the signal strength $AC_{ex}(x)$ and envelope $m_{ex}$ using the magnitude of the complex function $\tilde{I}_{ex}$:

$$AC_{ex}(x)m_{ex}[\zeta-h_{ex}(x)]=|\tilde{I}_{ex}(\zeta,x)|. \tag{120}$$

According to the underlying theory of the technique, we expect at least a meaningful portion of $m_{ex}$ to have the same general shape as $m_{temp}^j$ for the correct model, the only difference being the linear offset $h_{ex}$ and the scaling factor $AC_{ex}(x)$. We also expect the difference between the experimental and interference pattern template phase offsets $\phi_{ex}$, $\phi_{pat}^j$, respectively, to be linearly proportional to the height $h_{ex}$, for the correct model.

The task at hand is to locate a specific signal pattern represented by the interference pattern template $\tilde{I}_{pat}^j$, within an experimental data set $\tilde{I}_{ex}$, and determine how well of a match there is for each of the different models j. In what follows, we shall drop the index j, and note the matching analysis proceeds for each of the models.

The first step is to find the scan position $\zeta_{best}$ for which the shapes of the envelopes $m_{ex}$, $m_{pat}$ and $\phi_{ex}$, $\phi_{pat}$ are best matched. A viable approach is a merit function based on the normalized correlation of the interference pattern template with the signal within a segment of the scan defined by the window w:

$$\Pi(\zeta,x) = \frac{|\tilde{I}(\zeta,x)|^2}{\langle m_{pat}^2 \rangle \langle |\tilde{I}_{ex}(\zeta,x)|^2 \rangle} \quad \text{where} \tag{121}$$

$$\tilde{I}(\zeta,x) = \frac{1}{N}\int_{-\infty}^{\infty} \tilde{I}_{pat}^*(\hat{\zeta})\tilde{I}_{ex}(\zeta+\hat{\zeta},x)d\hat{\zeta}. \tag{122}$$

is the complex correlation function and $$\langle m_{pat}^2 \rangle = \frac{1}{N}\int_{-\infty}^{\infty}|\tilde{I}_{pat}(\hat{\zeta})|^2 d\hat{\zeta} \tag{123}$$

$$\langle|\tilde{I}_{ex}(\zeta,x)|^2\rangle = \frac{1}{N}\int_{-\infty}^{\infty}|\tilde{I}_{ex}(\zeta+\hat{\zeta},x)|^2 w(\hat{\zeta})d\hat{\zeta} \tag{124}$$

are normalizations that make the merit function $\Pi$ independent of signal-strength. Use of the complex conjugate $\tilde{I}^*_{pat}$ of the template cancels the synchronous linear phase term $K_0\zeta$ and maximizes $\Pi$ for the case of a match of $\phi_{ex}$, $\phi_{pat}$. The absolute value | | of the correlation removes any residual complex phase.

To prevent $\Pi(\zeta)$ from generating false high values or encountering a singularity at low signal levels, it is prudent to add a minimum value to the denominator, such as $$\langle|\tilde{I}_{ex}(\zeta)|^2\rangle \leftarrow \langle|\tilde{I}_{ex}(\zeta)|^2\rangle + \text{MinDenom}\cdot\max(\langle|\tilde{I}_{ex}|^2\rangle) \tag{125}$$

where the max( ) function returns the maximum value of the signal strength $|\tilde{I}_{ex}|$ over the full scan length $\zeta$, and MinDenom is the minimum relative signal strength that we consider valid in the merit function search. The value of MinDenom can be hard coded at 5% or some other small value, or left as an adjustable parameter.

The correlation integral $\tilde{I}$ can also be performed in the frequency domain using the correlation theorem:

$$\tilde{I}(\zeta)=FT^{-1}\{\tilde{q}^*_{pat}(K)\tilde{q}_{ex}(K)\} \tag{126}$$

where I have made use of $$FT\{\tilde{I}^*_{pat}(\zeta,x)\}=\tilde{q}^*_{pat}(-K,x) \tag{127}$$

where $$\tilde{q}_{pat}(K,x)=FT\{\tilde{I}_{pat}(\zeta,x)\}. \tag{128}$$

A search through $\Pi$ to find a peak value yields the best match position $\zeta_{best}$ and the value of $\Pi$ is a measure of the quality of the match, ranging from zero to one, with one corresponding to a perfect match. The peak value of the merit function is calculated for each of the different models to determine which model is the best match, and then the best match position $\zeta_{best}$ for that model gives the surface height.

Figure 20:
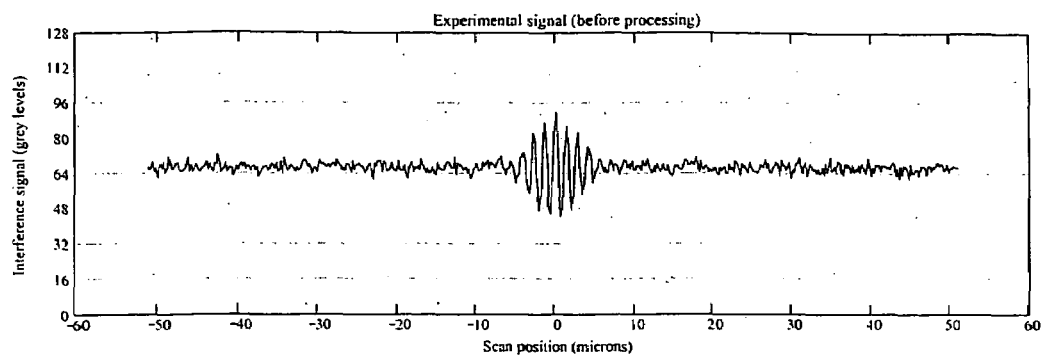
FIG. 20 shows an actual scanning interferometry signal of a base Si substrate without a thin film.
Figure 21:
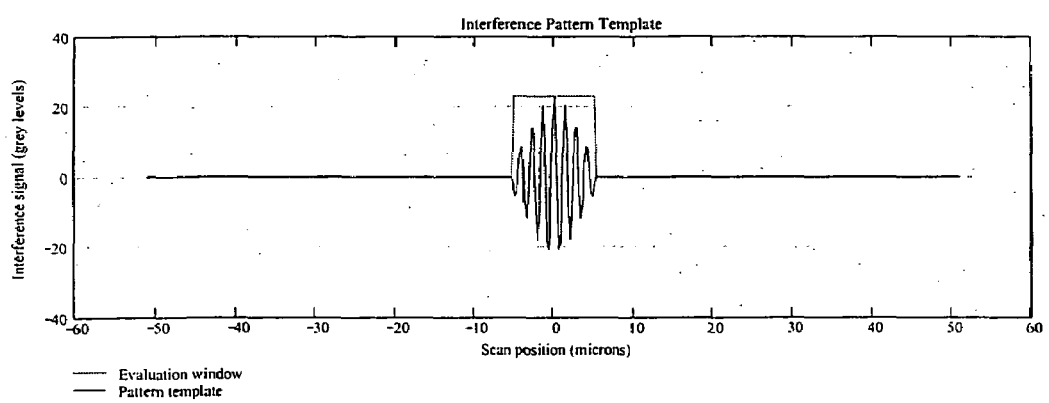
FIGS. 21 and 22 show interference template patterns for a bare Si substrate and a thin film structure with 1 micron of SiO2 on Si, respectively.
Figure 23:
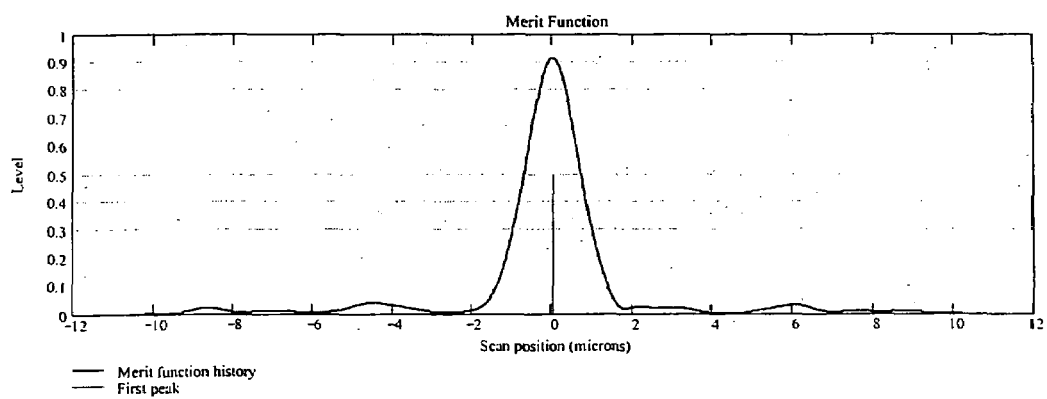
FIGS. 23 and 24 show the merit function as a function of scan positions for template functions in FIGS. 21 and 22, respectively.
Figure 22:
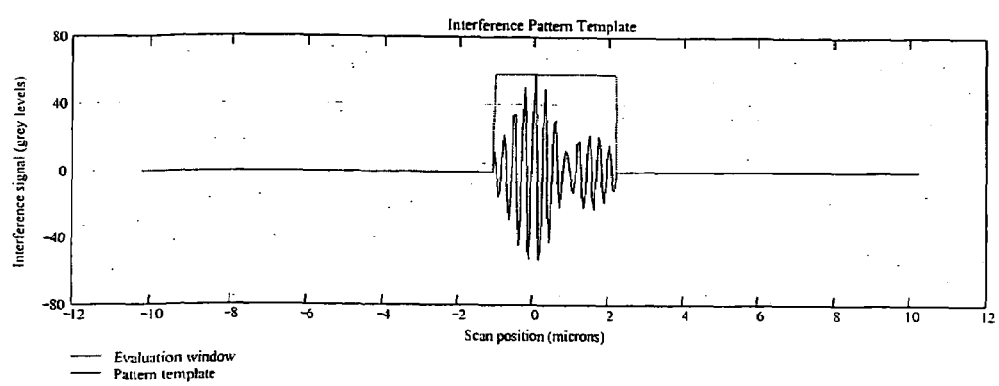
Figure 24:
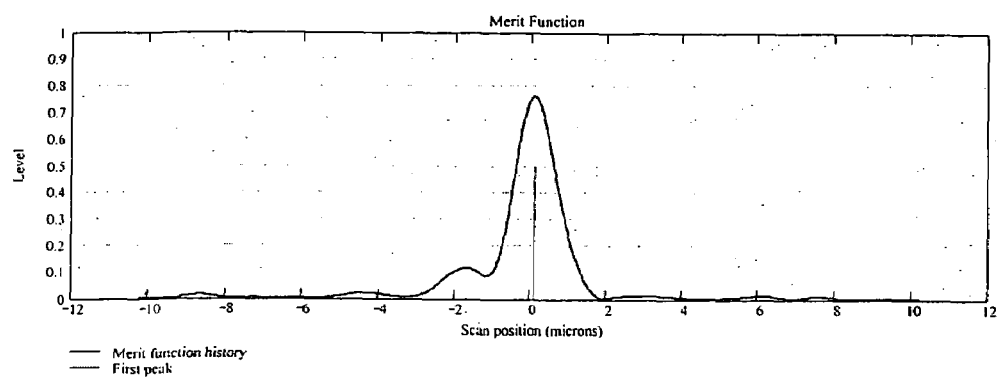

FIGS. 20–24 illustrate an example of the technique. FIG. 20 shows an actual scanning interferometry signal of a base Si substrate without a thin film. FIGS. 21 and 22 show interference template patterns for a bare Si substrate and a thin film structure with 1 micron of SiO2 on Si, respectively. FIGS. 23 and 24 show the merit function as a function of scan positions for template functions in FIGS. 21 and 22, respectively. The merit functions show that the interference template pattern for the bare substrate is a much better match (peak value 0.92) than that for the thin film template pattern (peak value 0.76) and therefore indicate that the test sample is a bare substrate. Moreover, the position of the peak in the merit function for the correct template pattern gives the relative surface height position for the test sample.

The methods and systems described above can be particularly useful in semiconductor applications. Additional embodiments of the invention include applying any of the measurement techniques described above to address any of the semiconductor applications described below, and systems for carrying out both the measurement techniques and the semiconductor applications.

It is presently of considerable interest in the semiconductor industry to make quantitative measurements of surface topography. Due to the small size of typical chip features, the instruments used to make these measurements typically must have high spatial resolution both parallel and perpendicular to the chip surface. Engineers and scientists use surface topography measuring systems for process control and to detect defects that occur in the course of manufacturing, especially as a result of processes such as etching, polishing, cleaning and patterning.

For process control and defect detection to be particularly useful, a surface topography measuring system should have lateral resolution comparable to the lateral size of typical surface features, and vertical resolution comparable to the minimum allowed surface step height. Typically, this requires a lateral resolution of less than a micron, and a vertical resolution of less than 1 nanometer. It is also preferable for such a system to make its measurements without contacting the surface of the chip, or otherwise exerting a potentially damaging force upon it, so as to avoid modifying the surface or introducing defects. Further, as it is well-known that the effects of many processes used in chip making depend strongly on local factors such as pattern density and edge proximity, it is also important for a surface topography measuring system to have high measuring throughput, and the ability to sample densely over large areas in regions which may contain one or many surface features of interest.

It is becoming common among chip makers to use the so-called 'dual damascene copper' process to fabricate electrical interconnects between different parts of a chip. This is an example of a process which may be effectively characterized using a suitable surface topography system. The dual damascene process may be considered to have five parts: (1) an interlayer dielectric (ILD) deposition, in which a layer of dielectric material (such as a polymer, or glass) is deposited onto the surface of a wafer (containing a plurality of individual chips); (2) chemical mechanical polishing (CMP), in which the dielectric layer is polished so as to create a smooth surface, suitable for precision optical lithography, (3) a combination of lithographic patterning and reactive ion etching steps, in which a complex network is created comprising narrow trenches running parallel to the wafer surface and small vias running from the bottom of the trenches to a lower (previously defined) electrically conducting layer, (4) a combination of metal deposition steps which result in the trenches and vias being over-filled with copper, and (5) a final chemical mechanical polishing (CMP) step in which the excess copper is removed, leaving a network of copper filled trenches (and possibly vias) surrounded by dielectric material.

Typically the thickness of the copper in the trench areas (i.e., the trench depth), and the thickness of the surrounding dielectric lie in a range of 0.2 to 0.5 microns. The width of the resulting trenches may be in a range of from 100 to 100,000 nanometers, and the copper regions within each chip may in some regions form regular patterns such as arrays of parallel lines, and in others they may have no apparent pattern. Likewise, within some regions the surface may be densely covered with copper regions, and in other regions, the copper regions may be sparse. It is important to appreciate that the polishing rate, and therefore the remaining copper (and dielectric) thickness after polishing, depends strongly and in a complex manner on the polishing conditions (such as the pad pressure and polishing slurry composition), as well as on the local detailed arrangement (i.e., orientation, proximity and shape) of copper and surrounding dielectric regions.

This 'position dependent polishing rate' is known to give rise to variable surface topography on many lateral length scales. For example, it may mean that chips located closer to the edge of a wafer on aggregate are polished more rapidly than those located close to the center, creating copper regions which are thinner than desired near the edges, and thicker than desired at the center. This is an example of a 'wafer scale' process nonuniformity—i.e., one occurring on a length scale comparable to the wafer diameter. It is also known that regions which have a high density of copper trenches polish at a higher rate than nearby regions with low copper line densities. This leads to a phenomenon known as 'CMP induced erosion' in the high copper density regions. This is an example of a 'chip scale' process nonuniformity—i.e., one occurring on a length scale comparable to (and sometimes much less than) the linear dimensions of a single chip. Another type of chip scale nonuniformity, known as 'dishing', occurs within single copper filled trench regions (which tend to polish at a higher rate than the surrounding dielectric material). For trenches greater than a few microns in width dishing may become severe with the result that affected lines later exhibit excessive electrical resistance, leading to a chip failure.

CMP induced wafer and chip scale process nonuniformities are inherently difficult to predict, and they are subject to change over time as conditions within the CMP processing system evolve. To effectively monitor, and suitably adjust the process conditions for the purpose of ensuring that any nonuniformities remain within acceptable limits, it is important for process engineers to make frequent non-contact surface topography measurements on chips at a large number and wide variety of locations. This is possible using embodiments of the interferometry techniques described above.

Any of the computer analysis methods described above can be implemented in hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein.

A number of embodiments of the invention have been described. Nevertheless, it will be understood that various modifications may be made without departing from the spirit and scope of the invention.

What is claimed is:

1. A method comprising:
comparing information derivable from a scanning interferometry signal for a first surface location of a test object to information corresponding to multiple models of the test object, wherein the multiple models are parametrized by a series of characteristics for the test object,
wherein the derivable information being compared relates to a shape of the scanning interferometry signal for the first surface location of the test object.

2. The method of claim 1, further comprising determining an accurate characteristic for the test object based on the comparison.

3. The method of claim 1, further comprising determining a relative surface height for the first surface location based on the comparison.

4. The method of claim 3, wherein the determining of the relative surface height comprises determining which model corresponds to an accurate one of the characteristic for the test object based on the comparison, and using the model corresponding to the accurate characteristic to calculate the relative surface height.

5. The method of claim 4, wherein using the model corresponding to the accurate characteristic to calculate the relative surface height comprises determining a position of a peak in a correlation function used to compare the information for the test object to the information for the model corresponding to the accurate characteristic.

6. The method of claim 1, further comprising comparing information derivable from the scanning interferometry signal for additional surface locations to the information corresponding to the multiple models.

7. The method of claim 6, further comprising determining a surface height profile for the test object based on the comparisons.

8. The method of claim 1, wherein the comparing comprises calculating one or more merit functions indicative of a similarity between the information derivable from the scanning interferometry signal and the information corresponding to each of the models.

9. The method of claim 1, wherein the comparing comprises fitting the information derivable from the scanning interferometry signal to an expression for the information corresponding to the models.

10. The method of claim 1, wherein the information for the test object relates to a fringe contrast magnitude in the shape of the scanning interferometry signal.

11. The method of claim 1, wherein the information for the test object relates to relative spacings between zero-crossings in the shape of the scanning interferometry signal.

12. The method of claim 1, wherein the information for the test object is a expressed as a function of scan position.

13. The method of claim 12, wherein the comparing comprises calculating a correlation function between the information for the test object and the information for each of the models.

14. The method of claim 12, wherein the comparing further comprises determining one or more peak values in each of the correlation functions.

15. The method of claim 14, further comprising determining an accurate characteristic for the test object based on the parameterization of the model corresponding to the largest peak value.

16. The method of claim 14, further comprising determining a relative surface height for the test object at the first surface location based on a coordinate for at least one of the peak values in the correlation functions.

17. The method of claim 1, wherein the scanning interferometry signal is produced by a scanning interferometry system, and wherein the comparing comprises accounting for systematic contributions to the scanning interferometry signal arising from the scanning interferometry system.

18. The method of claim 17, further comprising calibrating the systematic contributions of the scanning interferometry system using another test object having known properties.

19. The method of claim 1, wherein the series of characteristics comprises a series of values for at least one physical parameter of the test object.

20. The method of claim 19, wherein the test object comprises a thin film layer having a thickness, and the physical parameter is the thickness of the thin film at the first location.

21. The method of claim 1, wherein the series of characteristics comprises a series of characteristics of the test object at a second surface location different from the first surface location.

22. The method of claim 21, wherein the test object comprises structure at the second surface location that diffracts light to contribute to the scanning interferometry signal for the first surface location.

23. The method of claim 21, wherein the series of characteristics at the second surface location comprises permutations of a magnitude for a step height at the second location and a position for the second location.

24. The method of claim 21, wherein the series of characteristics at the second surface location comprises permutations of a modulation depth for a grating and an offset position of the grating, wherein the grating extends over the second location.

25. The method of claim 1, wherein the series of characteristics is a series of surface materials for the test object.

26. The method of claim 1, wherein the models correspond to a fixed surface height for the test object at the first surface location.

27. The method of claim 1, wherein the scanning interferometry signal is produced by imaging test light emerging from the test object to interfere with reference light on a detector, and varying an optical path length difference from a common source to the detector between interfering portions of the test and reference light, wherein the test and reference light are derived from the common source, and wherein the scanning interferometry signal corresponds to an interference intensity measured by the detector as the optical path length difference is varied.

28. The method of claim 27, further comprising producing the scanning interferometry signal.

29. The method of claim 27, wherein the test and reference light have a spectral bandwidth greater than 5% of a central frequency for the test and reference light.

30. The method of claim 27, wherein the common source has a spectral coherence length, and the optical path length difference is varied over a range larger than the spectral coherence length to produce the scanning interferometry signal.

31. The method of claim 27, wherein optics used to direct test light onto the test object and image it to the detector define a numerical aperture for the test light greater than 0.8.

32. The method of claim 28, wherein the common source is a spatially extended source.

33. Apparatus comprising:
a computer readable medium having a program that causes a processor in a computer to compare information derivable from a scanning interferometry signal for a first surface location of a test object to information corresponding to multiple models of the test object, wherein the multiple models are parametrized by a series of characteristics for the test object,
wherein the derivable information being compared relates to a shape of the scanning interferometry signal for the first surface location of the test object.

34. Apparatus comprising:
a scanning interferometry system configured to produce a scanning interferometry signal; and
an electronic processor coupled to the scanning interferometry system to receive the scanning interferometry signal and programmed to compare information derivable from a scanning interferometry signal for a first surface location of a test object to information corresponding to multiple models of the test object, wherein the multiple models are parametrized by a series of characteristics for the test object,
wherein the derivable information being compared relates to a shape of the scanning interferometry signal for the first surface location of the test object.

35. A method comprising:
comparing information derivable from a scanning interferometry signal for a first surface location of a test object to information corresponding to multiple models of the test object, wherein the multiple models are parametrized by a series of characteristics for the test object, wherein the series of characteristics comprises a series of characteristics of the test object at a second surface location different from the first surface location.

36. The method of claim 35, wherein the test object comprises structure at the second surface location that diffracts light to contribute to the scanning interferometry signal for the first surface location.

37. The method of claim 35, wherein the series of characteristics at the second surface location comprises permutations of a magnitude for a step height at the second location and a position for the second location.

38. The method of claim 35, wherein the series of characteristics at the second surface location comprises permutations of a modulation depth for a grating and an offset position of the grating, wherein the grating extends over the second location.

39. The method of claim 35, further comprising determining an accurate characteristic for the test object based on the comparison.

40. The method of claim 35, further comprising determining a relative surface height for the first surface location based on the comparison.

41. The method of claim 40, wherein the determining of the relative surface height comprises determining which model corresponds to an accurate one of the characteristic for the test object based on the comparison, and using the model corresponding to the accurate characteristic to calculate the relative surface height.

42. The method of claim 41, wherein the using of the model corresponding to the accurate characteristic comprises compensating data from the scanning interferometry signal to reduce contributions arising from the accurate characteristic.

43. The method of claim 42, wherein the compensating of the data comprises removing a phase contribution arising from the accurate characteristic from a phase component of a transform of the scanning interferometry signal for the test object, and wherein the using of the model corresponding to the accurate characteristic further comprises calculating the relative surface height from the phase component of the transform after the phase contribution arising from the accurate characteristic has been removed.

44. The method of claim 42, wherein using the model corresponding to the accurate characteristic to calculate the relative surface height comprises determining a position of a peak in a correlation function used to compare the information for the test object to the information for the model corresponding to the accurate characteristic.

45. The method of claim 35, further comprising comparing information derivable from the scanning interferometry signal for additional surface locations to the information corresponding to the multiple models.

46. The method of claim 45, further comprising determining a surface height profile for the test object based on the comparisons.

47. The method of claim 35, wherein the comparing comprises calculating one or more merit functions indicative of a similarity between the information derivable from the scanning interferometry signal and the information corresponding to each of the models.

48. The method of claim 35, wherein the comparing comprises fitting the information derivable from the scanning interferometry signal to an expression for the information corresponding to the models.

49. The method of claim 35, wherein the information derivable from the scanning interferometry signal and which is being compared is a number.

50. The method of claim 35, wherein the information derivable from the scanning interferometry signal and which is being compared is a function.

51. The method of claim 50, wherein the function is a function of spatial frequency.

52. The method of claim 50, wherein the function is a function of scan position.

53. The method of claim 35, wherein the information for the test object is derived from a transform of the scanning interferometry signal for the test object into a spatial frequency domain.

54. The method of claim 53, wherein the transform is a Fourier transform.

55. The method of claim 53, wherein the information for the test object comprises information about an amplitude profile of the transform.

56. The method of claim 53, wherein the information for the test object comprises information about a phase profile of the transform.

57. The method of claim 35, wherein information for the test object relates to a shape of the scanning interferometry signal for the test object at the first location.

58. The method of claim 57, wherein the information for the test object relates to a fringe contrast magnitude in the shape of the scanning interferometry signal.

59. The method of claim 57, wherein the information for the test object relates to relative spacings between zero-crossings in the shape of the scanning interferometry signal.

60. The method of claim 57, wherein the information for the test object is a expressed as a function of scan position, wherein the function is derived from the shape of the scanning interferometry signal.

61. The method of claim 35, wherein the comparing comprises calculating a correlation function between the information for the test object and the information for each of the models.

62. The method of claim 61, wherein the correlation function is a complex correlation function.

63. The method of claim 61, wherein the comparing further comprises determining one or more peak values in each of the correlation functions.

64. The method of claim 63, further comprising determining an accurate characteristic for the test object based on the parameterization of the model corresponding to the largest peak value.

65. The method of claim 63, further comprising determining a relative surface height for the test object at the first surface location based on a coordinate for at least one of the peak values in the correlation functions.

66. The method of claim 35, wherein the scanning interferometry signal is produced by a scanning interferometry system, and wherein the comparing comprises accounting for systematic contributions to the scanning interferometry signal arising from the scanning interferometry system.

67. The method of claim 66, further comprising calibrating the systematic contributions of the scanning interferometry system using another test object having known properties.

68. Apparatus comprising:
a computer readable medium having a program that causes a processor in a computer to compare information derivable from a scanning interferometry signal for a first surface location of a test object to information corresponding to multiple models of the test object, wherein the multiple models are parametrized by a series of characteristics for the test object, wherein the series of characteristics comprises a series of characteristics of the test object at a second surface location different from the first surface location.

69. Apparatus comprising:

a scanning interferometry system configured to produce a scanning interferometry signal; and an electronic processor coupled to the scanning interferometry system to receive the scanning interferometry signal and programmed to compare information derivable from a scanning interferometry signal for a first surface location of a test object to information corresponding to multiple models of the test object, wherein the multiple models are parametrized by a series of characteristics for the test object, wherein the series of characteristics comprises a series of characteristics of the test object at a second surface location different from the first surface location.

70. A method comprising:

chemically mechanically polishing a test object;

collecting scanning interferometry data for a surface topography of the test object; and adjusting process conditions for the chemically mechanically polishing of the test object based on information derived from the scanning interferometry data, wherein adjusting the process conditions based on the information derived from the scanning interferometry data comprises comparing information derivable from the scanning interferometry signal for at least a first surface location of a test object to information corresponding to multiple models of the test object, wherein the multiple models are parameterized by a series of characteristics for the test object.

71. The method of claim 70, where the process conditions comprise at least one of pad pressure and polishing slurry composition.

* * * * *

UNITED STATES PATENT AND TRADEMARK OFFICE
CERTIFICATE OF CORRECTION

PATENT NO.         : 7,106,454 B2
APPLICATION NO. : 10/795808
DATED              : September 12, 2006
INVENTOR(S)        : Peter De Groot, Robert Stoner and Xavier Colonna De Lega It is certified that error appears in the above-identified patent and that said Letters Patent is hereby corrected as shown below:

Column 2
Line 26, delete "that" after "about"

Column 3
Line 54, insert --a-- before "second"

Column 5
Line 16, replace "profiled" with --profile--
Line 37, delete "a" after "to"

Column 6
Line 28, insert --be-- after "may"

Column 8
Line 18, replace "signals" with --signal--

Column 9
Line 56, replace "displays" with --display--
Line 57, replace "transmits" with --transmit--

Column 10
Line 57, replace "objectives" with --objective--

Column 13
Line 54, insert --be-- after "may"

Column 14
Line 63, delete "is" after "polarizer"

Column 19
Line 25, replace "that" with --than--

Column 21
Line 66, replace "$q_{\beta,k} = q_{\beta,k}^{s} + q_{\beta,k}^{p}$" with -- $q_{\beta,k} = q_{\beta,k}^{s} + q_{\beta,k}^{p}$ --

UNITED STATES PATENT AND TRADEMARK OFFICE
CERTIFICATE OF CORRECTION

PATENT NO. : 7,106,454 B2
APPLICATION NO. : 10/795808
DATED : September 12, 2006
INVENTOR(S) : Peter De Groot, Robert Stoner and Xavier Colonna De Lega It is certified that error appears in the above-identified patent and that said Letters Patent is hereby corrected as shown below:

Column 22
Line 4, replace " $\langle \phi''_{\beta,k} \rangle = \arg(q_{\beta,k}{}^s + q_{\beta,k}{}^p)$ " with -- $\langle \phi''_{\beta,k} \rangle = \arg(q^s_{\beta,k} + q^p_{\beta,k})$ --

Line 8, replace " $\langle \phi''_{\beta,k} \rangle \neq (\phi''_{\beta,k}{}^s + \phi''_{\beta,k}{}^p)/2$ " with -- $\langle \phi''_{\beta,k} \rangle \neq (\phi''^s_{\beta,k} + \phi''^p_{\beta,k})/2$ --

Line 12, replace " $\langle Q_{\beta,k} \rangle \neq (Q_{\beta,k}{}^s + Q_{\beta,k}{}^p)/2$ " with -- $\langle Q_{\beta,k} \rangle \neq (Q^s_{\beta,k} + Q^p_{\beta,k})/2$ --

Line 15, replace " $R_{\beta,k}{}^s, R_{\beta,k}{}^p$ and $Z_{\beta,k}{}^s, Z_{\beta,k}{}^p$ " with -- $R^s_{\beta,k}, R^p_{\beta,k}$ and $Z^s_{\beta,k}, Z^p_{\beta,k}$ --

Column 23
Line 23, insert --are-- after "we"

Column 24

Line 25, replace "
$$\vartheta^p_{1,\beta,k} = -\frac{\tan(\psi_0 - \psi_{1,\beta,k})}{\tan(\psi_0 + \psi_{1,\beta,k})}$$
" with -- $$\vartheta^p_{1,\beta,k} = -\frac{\sin(\psi_0 - \psi_{1,\beta,k})}{\sin(\psi_0 + \psi_{1,\beta,k})}$$ --

Line 38, replace " $\vartheta^s_{2,\beta,k} = -\frac{\tan(\psi_{1,\beta,k} - \psi_{2,\beta,k})}{\tan(\psi_{1,\beta,k} + \psi_{2,\beta,k})}$ " with -- $\vartheta^s_{2,\beta,k} = -\frac{\sin(\psi_{1,\beta,k} - \psi_{2,\beta,k})}{\sin(\psi_{1,\beta,k} + \psi_{2,\beta,k})}$ --

Line 47, replace "$z_{\beta,k} = \theta_{1,\beta,k}$    (simple surface, no thin film)" with --$z_{\beta,k} = \vartheta_{1,\beta,k}$    (simple surface, no thin film)--

Line 52, replace "$\omega_{\beta,k} = \arg(\theta_{1,\beta,k})$" with -- $\omega_{\beta,k} = \arg(\vartheta_{1,\beta,k})$ --

Column 27
Line 8, replace "100xMirau" with --100X MIRAU--

UNITED STATES PATENT AND TRADEMARK OFFICE
CERTIFICATE OF CORRECTION

PATENT NO. : 7,106,454 B2  Page 3 of 4
APPLICATION NO. : 10/795808
DATED : September 12, 2006
INVENTOR(S) : Peter De Groot, Robert Stoner and Xavier Colonna De Lega It is certified that error appears in the above-identified patent and that said Letters Patent is hereby corrected as shown below:

Column 29
Line 10, replace "40 mm" with --40 nm--
Line 11, replace "498 mm" with --498 nm--
Line 21, replace "300 run" with --300 nm--
Line 52, replace "removes" with --remove--

Column 30
Line 23, replace "$q_{K>0}{}^{ex} = M^{-1} \exp[-i\gamma_{sys} - i(K-K0)\tau_{sys}]q_{K>0}{}^{ex}$" with -- $q_{K>0}^{ex} = M^{-1} \exp\left[-i\gamma_{sys} - i(K-K0)\tau_{sys}\right]q_{K>0}^{ex}$ --

Line 33, replace "functions" with --function--
Line 50, replace "$\Gamma_{sys} = K0\ h''$" with --$\gamma_{sys} = K0\ h'$--

Column 31
Line 49, replace "signals in" with --signals--

Column 32
Line 48, replace "consider to" with --consider--
Line 56, delete "a"

Column 33
Line 1, insert "be" after "can"
Line 26, replace "analysis the" with --analysis that--
Line 54, delete "be" after "would"

Column 34
Line 5, replace "$I_{temp}{}^{j}(\zeta) = m_{temp}{}^{j}(\zeta)\cos[K_0\zeta + \phi_{temp}{}^{j}(\zeta)]$" with -- $I_{temp}^{j}(\zeta) = m_{temp}^{j}(\zeta)\cos\left[K_0\zeta + \varphi_{temp}^{j}(\zeta)\right]$ --

Line 7, replace "$m_{temp}{}^{j}(\zeta)$ and $\phi_{temp}{}^{j}(\zeta)$" with -- $m_{temp}^{j}(\zeta)$ and $\varphi_{temp}^{j}(\zeta)$ --

Line 11, replace "$m_{temp}{}^{j}(\zeta)$ and $\phi_{temp}{}^{j}(\zeta)$" with -- $m_{temp}^{j}(\zeta)$ and $\varphi_{temp}^{j}(\zeta)$ --

Line 15, replace " $\tilde{I}_{temp}{}^{j}(\zeta) = m_{temp}{}^{j}(\zeta)\exp\left[i\left(K_0\zeta + \varphi_{temp}{}^{j}(\zeta)\right)\right]$ " with -- $\tilde{I}_{temp}^{j}(\zeta) = m_{temp}^{j}(\zeta)\exp\left[i\left(K_0\zeta + \varphi_{temp}^{j}(\zeta)\right)\right]$ --

UNITED STATES PATENT AND TRADEMARK OFFICE
CERTIFICATE OF CORRECTION

PATENT NO. : 7,106,454 B2
APPLICATION NO. : 10/795808
DATED : September 12, 2006
INVENTOR(S) : Peter De Groot, Robert Stoner and Xavier Colonna De Lega It is certified that error appears in the above-identified patent and that said Letters Patent is hereby corrected as shown below:

Column 34 Cont.

Line 25, replace " $\tilde{I}_{pat}{}^k(\zeta) = w(\zeta)\overline{I}_{temp}{}^k(\zeta)$ " with -- $\tilde{I}^k_{pat}(\zeta) = w(\zeta)\overline{I}^k_{temp}(\zeta)$ --

Line 37, replace " $\tilde{I}_{pat}{}^j$ " with -- $\tilde{I}^j_{pat}$ --

Column 35
Line 8, replace "$m_{temp}{}^j$" with -- $m^j_{temp}$ --

Lines 11 and 12, replace "$\phi_{ex}, \phi_{pat}{}^j$" with --$\varphi_{ex}, \varphi^j_{pat}$ --

Line 15, replace " $\tilde{I}_{pat}{}^j$ " with -- $\tilde{I}^j_{pat}$ --

Line 56, replace " $\langle|\tilde{I}_{ex}(\zeta)|^2\rangle \leftarrow \langle|\tilde{I}_{ex}(\zeta)|^2\rangle + MinDenom \cdot \max(<|\tilde{I}_{ex}|^2>)$ " with -- $\langle|\tilde{I}_{ex}(\zeta)|^2\rangle \leftarrow \langle|\tilde{I}_{ex}(\zeta)|^2\rangle + MinDenom \cdot \max\left(\langle|\tilde{I}_{ex}|^2\rangle\right)$ --

Column 39
Claim 12, line 24, delete "a" before "expressed"

Column 42
Claim 60, line 30, delete "a" before "expressed"

Signed and Sealed this

Tenth Day of June, 2008

JON W. DUDAS
*Director of the United States Patent and Trademark Office*